US012779024B2

(12) United States Patent
Yang et al.

(10) Patent No.: US 12,779,024 B2
(45) **Date of Patent: *Nov. 3, 2026**

(54) HUMAN CD276-TARGETING MONOCLONAL ANTIBODY AND APPLICATION THEREOF

(71) Applicant: PERSONGEN BIOTHERAPEUTICS (SUZHOU) CO., LTD., Suzhou (CN)

(72) Inventors: Lin Yang, Suzhou (CN); Fengtao You, Suzhou (CN)

(73) Assignee: PERSONGEN BIOTHERAPEUTICS (SUZHOU) CO., LTD., Jiangsu (CN)

( * ) Notice: Subject to any disclaimer, the term of this patent is extended or adjusted under 35 U.S.C. 154(b) by 668 days.

This patent is subject to a terminal disclaimer.

(21) Appl. No.: 18/261,398

(22) PCT Filed: Dec. 24, 2021

(86) PCT No.: PCT/CN2021/141337

§ 371 (c)(1), (2) Date: Jan. 19, 2024

(87) PCT Pub. No.: WO2022/151958

PCT Pub. Date: Jul. 21, 2022

(65) Prior Publication Data

US 2025/0002583 A1 Jan. 2, 2025

(30) Foreign Application Priority Data

Jan. 13, 2021 (CN) ......................... 202110044547.1

(51) Int. Cl.

*A61K 39/00* (2006.01)
*C07K 16/28* (2006.01)
*C12N 5/0783* (2010.01)

(52) U.S. Cl.

CPC ....... *A61K 39/001111* (2018.08); *A61K 39/00* (2013.01); *C07K 16/2827* (2013.01); *C12N 5/0636* (2013.01); *C12N 5/0646* (2013.01); *A61K 2039/5156* (2013.01); *C07K 2317/24* (2013.01); *C07K 2317/565* (2013.01); *C07K 2317/622* (2013.01); *C07K 2317/92* (2013.01)

(58) Field of Classification Search

None

See application file for complete search history.

(56) References Cited

FOREIGN PATENT DOCUMENTS

| | | | | | |
|---|---|---|---|---|---|
| CN | 109609533 | A | * | 4/2019 | ............. C12N 15/86 |
| CN | 109929039 | A | | 6/2019 | |
| CN | 110305213 | A | * | 10/2019 | ......... A61K 31/4045 |
| CN | 110950953 | A | | 4/2020 | |
| WO | 2017180813 | A1 | | 10/2017 | |
| WO | 2017214335 | A1 | | 12/2017 | |
| WO | 2020103100 | A1 | | 5/2020 | |

OTHER PUBLICATIONS

The extended European search report issued in European Application No. 21919145.9, dated Jul. 12, 2024.

Rizvi et al. "A phase 1 study of enoblituzumab in combination with pembrolizumab in patients with advanced B7-H3-expressing cancers. ". Journal of Clinical Oncology, vol. 34, No. 15_suppl, May 20, 2016, cited in EESR.

Ahmed et al., "Humanized Affinity-matured Monoclonal Antibody 8H9 Has Potent Antitumor Activity and Binds to FG Loop of Tumor Antigen B7-H3" Journal of Biological Chemistry, vol. 290, No. 50, pp. 30018-30029, Dec. 11, 2015, cited in EESR.

International Search Report (with English translation) and Written Opinion issued in PCT/CN2021/141337, dated Mar. 24, 2022, 16 pages provided.

* cited by examiner

*Primary Examiner* — Maher M Haddad
(74) *Attorney, Agent, or Firm* — HSML P.C.

(57) ABSTRACT

Provided are a human CD276-targeting monoclonal antibody and an application thereof. Specifically, provided are a CD276-targeting antibody, which has a high affinity and a high specificity for human CD276. Further provided are a pharmaceutical composition and a cell containing the antibody, as well as a preparation method for the antibody and an application.

9 Claims, 15 Drawing Sheets

Specification includes a Sequence Listing.

HUMAN CD276-TARGETING MONOCLONAL ANTIBODY AND APPLICATION THEREOF

TECHNICAL FIELD

The present invention relates to the field of biomedicine, and more particularly to a human CD276-targeting monoclonal antibody and application thereof.

BACKGROUND

CD276 molecule, also known as B7-H3 molecule, is a kind of recently discovered type I transmembrane glycoprotein, belonging to the B7 immune costimulatory and co-inhibitory globulin family. Human B7-H3 molecule has two subtypes, 2Ig-B7-H3 and 4Ig-B7H3. Murine B7-H3 has only one subtype 2Ig-B7-H3, which is homologous with 88% of the amino acid sequence to human 2Ig-B7-H3 subtype. At present, the function of B7-H3 molecules is still going to be further elucidated, but the existing studies show that B7-H3 molecules have both immune activation and immunosuppressive effects. On one hand, the B7-H3 molecule can play an immunosuppressive effect by weakening the secretion of type I cytokine IFN-gamma, and many research results support that B7-H3 has a negative immunomodulatory effect in graft versus host disease, heart transplant rejection, airway inflammation and autoimmune encephalomyelitis model. On the other hand, B7-H3 is also found to exert a function of providing an immune co-stimulatory signal for T cells in autoimmune diseases in vivo and in vitro.

A large number of studies show that B7-H3 is overexpressed in various human tumors, including leukemia, gastric cancer, breast cancer, non-small cell lung cancer, ovarian cancer, osteosarcoma, neuroblastoma, pancreatic cancer, breast cancer and the like, but has only limited expression in normal tissue. At the same time, it is also reported to be expressed in important tumor microenvironment components such as tumor stem cells, tumor stromal cells and neovessels. The overexpression of B7-H3 can generally reduce the infiltration of tumor-associated lymphocytes in tumors and accelerate disease progression, and is generally closely related to the poor prognosis of cancers such as pancreatic ductal cancer, prostate cancer, ovarian cancer, lung cancer and transparent cell renal cancer.

At present, there are still many deficiencies in the study of B7-H3 monoclonal antibodies. It is necessary to develop a new B7-H3 monoclonal antibody and uses thereof in the art.

SUMMARY OF THE INVENTION

The purpose of the present invention is to provide a human CD276-targeting monoclonal antibody and application thereof.

In the first aspect of the present invention, it provides a heavy chain variable region of an antibody, which comprises following three complementarity determining regions (CDRs):

a CDR1 set forth in SEQ ID NO: 1, a CDR2 set forth in SEQ ID NO: 2, and a CDR3 set forth in SEQ ID NO: 3 or 7.

In another preferred embodiment, any one of the above amino acid sequences further includes a derivative sequence which is optionally added, deleted, modified, and/or substituted with at least one (e.g. 1-3, preferably 1-2 and more preferably 1) amino acid, and can retain the binding affinity to CD276.

In another preferred embodiment, the heavy chain variable region further comprises a human FR or a murine FR.

In another preferred embodiment, the heavy chain variable region has an amino acid sequence as shown in SEQ ID NO: 8 or 9.

In another preferred embodiment, the heavy chain variable region has an amino acid sequence as shown in SEQ ID NOs: 26-30.

In the second aspect of the present invention, it provides a heavy chain of an antibody, which comprises the heavy chain variable region according to the first aspect of the present invention.

In another preferred embodiment, the heavy chain of an antibody further comprises a heavy chain constant region.

In another preferred embodiment, the heavy chain constant region is of human origin, murine origin or rabbit origin.

In the third aspect of the present invention, it provides a light chain variable region of an antibody, which comprises following three complementarity determining regions (CDRs):

a CDR1' set forth in SEQ ID NO: 4, a CDR2' set forth in SEQ ID NO: 5, and a CDR3' set forth in SEQ ID NO: 6.

In another preferred embodiment, any one of the above amino acid sequences further includes a derivative sequence which is optionally added, deleted, modified, and/or substituted with at least one (e.g. 1-3, preferably 1-2 and more preferably 1) amino acid, and can retain the binding affinity to CD276.

In another preferred embodiment, the light chain variable region further comprises a human FR or a murine FR.

In another preferred embodiment, the light chain variable region has an amino acid sequence as shown in SEQ ID NO: 10.

In another preferred embodiment, the light chain variable region has an amino acid sequence as shown in SEQ ID NOs: 21-25.

In the fourth aspect of the present invention, it provides a light chain of an antibody, which comprises the heavy chain variable region according to the third aspect of the present invention.

In another preferred embodiment, the light chain of an antibody further comprises a light chain constant region.

In another preferred embodiment, the light chain constant region is of human origin, murine origin or rabbit origin.

In the fifth aspect of the present invention, it provides an antibody targeting CD276, which comprises:

(1) the heavy chain variable region according to the first aspect of the present invention; and/or (2) the light chain variable region according to the third aspect of the present invention;

or the antibody comprises the heavy chain according to the second aspect of the present invention; and/or the light chain according to the fourth aspect of the present invention.

In another preferred embodiment, the affinity constant KD (M) of the antibody for binding to human CD276 protein (preferably of wild type) is $(1\text{-}15)\times10^{8}$, and preferably $(5\text{-}12)\times10^{8}$.

In another preferred embodiment, the antibody binds to amino acids of positions 31-40 at the N-terminus of the human CD276 protein.

In another preferred embodiment, the antibody is selected from the group consisting of an animal-derived antibody, a chimeric antibody, a humanized antibody, and a combination thereof.

In another preferred embodiment, the antibody is a double-chain antibody or a single-chain antibody.

In another preferred embodiment, the antibody is a monoclonal antibody.

In another preferred embodiment, the antibody is a partially or fully humanized antibody.

In another preferred embodiment, the sequence of the heavy chain variable region of the antibody is shown in SEQ ID NO: 8 or 9; and/or the sequence of the light chain variable region of the antibody is shown in SEQ ID NO: 10.

In another preferred embodiment, the sequence of the heavy chain variable region of the antibody is shown in SEQ ID NO: 26, and the sequence of the light chain variable region of the antibody is shown in SEQ ID NO: 21.

In another preferred embodiment, the sequence of the heavy chain variable region of the antibody is shown in SEQ ID NO: 29, and the sequence of the light chain variable region of the antibody is shown in SEQ ID NO: 24.

In the sixth aspect of the present invention, it provides a recombinant protein, wherein the recombinant protein comprises:

(1) the heavy chain variable region according to the first aspect of the present invention, the heavy chain according to the second aspect of the present invention, the light chain variable region according to the third aspect of the present invention, the light chain according to the fourth aspect of the present invention, or the antibody according to the fifth aspect of the present invention; and (ii) an optional tag sequence to assist expression and/or purification.

In another preferred embodiment, the tag sequence comprises a 6His tag.

In another preferred embodiment, the recombinant protein (or polypeptide) comprises a fusion protein.

In another preferred embodiment, the recombinant protein is a monomer, dimer, or multimer.

In the seventh aspect of the present invention, it provides a CAR construct, wherein the scFv fragment of the monoclonal antibody antigen-binding domain of the CAR construct is a binding region specifically binding to CD276, and the scFv comprises the heavy chain variable region according to the first aspect of the present invention and the light chain variable region according to the third aspect of the present invention.

In another preferred embodiment, the CAR has a structure shown in the following Formula I:

$$\text{L-scFv-H-TM-C-CD3}\zeta \qquad \text{(I)}$$

wherein, each "-" is independently a linking peptide or peptide bond;

L is absent or a signal peptide sequence;

scFv is a scFv targeting CD276;

H is an optional hinge region;

TM is a transmembrane domain;

C is a co-stimulatory signaling molecule;

CD3ζ is a CD3ζ cytoplasmic signal transduction sequence.

In the eighth aspect of the present invention, it provides a recombinant immune cell, wherein the immune cell expresses an exogenous CAR construct according to the seventh aspect of the present invention.

In another preferred embodiment, the immune cell is selected from the group consisting of: NK cells and T cells.

In another preferred embodiment, the immune cell is derived from human or a non-human mammal (such as a mouse).

In the ninth aspect of the present invention, it provides an antibody-drug conjugate, wherein the antibody-drug conjugate comprises:

(a) an antibody moiety, wherein the antibody moiety is selected from the group consisting of: the heavy chain variable region according to the first aspect of the present invention, the heavy chain according to the second aspect of the present invention, the light chain variable region according to the third aspect of the present invention, the light chain according to the fourth aspect of the present invention, and the antibody according to the fifth aspect of the present invention, and a combination thereof; and (b) a coupling moiety coupled to the antibody moiety, which is selected from the group consisting of a detectable label, a drug, a toxin, a cytokine, a radionuclide, an enzyme, and a combination thereof.

In another preferred embodiment, the antibody moiety and the coupling moiety are coupled through a chemical bond or a linker.

In the tenth aspect of the present invention, it provides a use of an active ingredient selected from the group consisting of: the heavy chain variable region according to the first aspect of the present invention, the heavy chain according to the second aspect of the present invention, the light chain variable region according to the third aspect of the present invention, the light chain according to the fourth aspect of the present invention, the antibody according to the fifth aspect of the present invention, the recombinant protein according to the sixth aspect of the present invention, the immune cell according to the eighth aspect of the present invention, the antibody-drug conjugate according to the ninth aspect of the present invention, and combinations thereof, wherein the active ingredient is used for (a) preparation of a detection reagent or kit; and/or (b) preparation of a medicament for the prevention and/or treatment of a CD276-related disease.

In another preferred embodiment, the CD276-related disease includes a tumor and autoimmune disease.

In another preferred embodiment, the tumor is a CD276-positive tumor.

In another preferred embodiment, the tumor is selected from the group consisting of: a hematological tumor, solid tumor, and a combination thereof.

In another preferred embodiment, the hematological tumor is selected from the group consisting of: acute myeloid leukemia (AML), multiple myeloma (MM), chronic lymphocytic leukemia (CLL), acute lymphocytic leukemia (ALL), diffuse large B cell lymphoma (DLBCL), and a combination thereof.

In another preferred embodiment, the solid tumor is selected from the group consisting of gastric cancer, gastric cancer peritoneal metastasis, liver cancer, kidney tumor, lung cancer, small intestinal cancer, bone cancer, prostate cancer, colorectal cancer, breast cancer, colorectal cancer, cervical cancer, ovarian cancer, lymphoma, nasopharyngeal cancer, adrenal tumor, bladder tumor, non-small cell lung cancer (NSCLC), brain glioma, endometrial cancer, testicular cancer, colorectal cancer, urinary tract tumor, thyroid cancer, and a combination thereof.

In another preferred embodiment, the tumor is a gastric cancer, a breast cancer, or an osteosarcoma.

In another preferred embodiment, the antibody is in the form of a drug conjugate (ADC).

In another preferred embodiment, the detection reagent or kit is used for:

(1) detection of CD276 protein in a sample; and/or (2) detection of endogenous CD276 protein in tumor cells; and/or (3) detection of tumor cells expressing CD276 protein.

In another preferred embodiment, the detection reagent is a detection slide.

In the eleventh aspect of the present invention, it provides a pharmaceutical composition, wherein the pharmaceutical composition comprises:

(i) an active ingredient, wherein the active ingredient is selected from the group consisting of: the heavy chain variable region according to the first aspect of the present invention, the heavy chain according to the second aspect of the present invention, the light chain variable region according to the third aspect of the present invention, the light chain according to the fourth aspect of the present invention, the antibody according to the fifth aspect of the present invention, the recombinant protein according to the sixth aspect of the present invention, the immune cell according to the eighth aspect of the present invention, the antibody-drug conjugate according to the ninth aspect of the present invention, and a combination thereof; and (ii) a pharmaceutically acceptable carrier.

In another preferred embodiment, the pharmaceutical composition is a liquid preparation.

In another preferred embodiment, the pharmaceutical composition is an injection.

In the twelfth aspect of the present invention, it provides a polynucleotide, which encodes a polypeptide selected from the group consisting of:

(1) the heavy chain variable region according to the first aspect of the present invention, the heavy chain according to the second aspect of the present invention, the light chain variable region according to the third aspect of the present invention, the light chain according to the fourth aspect of the present invention, or the antibody according to the fifth aspect of the present invention; or (2) the recombinant protein according to the sixth aspect of the present invention;

(3) the CAR construct according to the seventh aspect of the present invention.

In another preferred embodiment, the nucleotide sequence is shown in SEQ ID NOs: 11-20.

In the thirteenth aspect of the present invention, it provides a vector, which contains the polynucleotide according to the twelfth aspect of the present invention.

In another preferred embodiment, the vector includes: bacterial plasmid, phage, yeast plasmid, plant cell virus, and mammalian cell virus such as adenovirus, retrovirus, or other vectors.

In the fourteenth aspect of the present invention, it provides a genetically engineered host cell, wherein the host cell comprises the vector according to the thirteenth aspect of the present invention or has the polynucleotide according to the twelfth aspect of the present invention integrated into its genome.

In the fifteenth aspect of the present invention, it provides a method for detection (including diagnostic or non-diagnostic) of CD276 protein in a sample in vitro, wherein the method comprises the steps:

(1) contacting the sample with the antibody according to the fifth aspect of the present invention or the antibody conjugate according to the ninth aspect of the present invention in vitro;

(2) detecting whether an antigen-antibody complex is formed, wherein the formation of the complex indicates the presence of CD276 protein in the sample.

In another preferred embodiment, the method is non-diagnostic and non-therapeutic.

In the sixteenth aspect of the present invention, it provides a detection plate, wherein the detection plate comprises a substrate (supporting plate) and a test strip, and the test strip contains the antibody according to the fifth aspect of the present invention or the antibody conjugate according to the ninth aspect of the present invention.

In the seventeenth aspect of the present invention, it provides a kit, which comprises:

(1) a first container, which contains the antibody according to the fifth aspect of the present invention; and/or (2) a second container, which contains a secondary antibody against the antibody according to the fifth aspect of the present invention;

or, the kit comprises the detection plate according to the sixteenth aspect of the present invention.

In the eighteenth aspect of the present invention, it provides a method for preparing a recombinant polypeptide, which comprises:

(a) culturing the host cell according to the fourteenth aspect of the present invention under conditions suitable for expression;

(b) isolating a recombinant polypeptide from the culture, wherein the recombinant polypeptide is the antibody according to the fifth aspect of the present invention or the recombinant protein according to the sixth aspect of the present invention.

In the nineteenth aspect of the present invention, it provides a method for preventing and/or treating CD276 related diseases, wherein the method comprises: administering the antibody according to the fifth aspect of the present invention, an antibody-drug conjugate of the antibody, or a CAR-T cell expressing the antibody, or a combination thereof to a subject in need thereof.

In another preferred embodiment, the method further comprises: administering other drugs or therapies to the subject in need thereof for a combined treatment.

It should be understood that, within the scope of the present invention, the technical features specifically described above and below (such as the Examples) can be combined with each other, thereby constituting a new or preferred technical solution which needs not be described one by one.

DETAILED DESCRIPTION OF EMBODIMENTS

Figure 1:
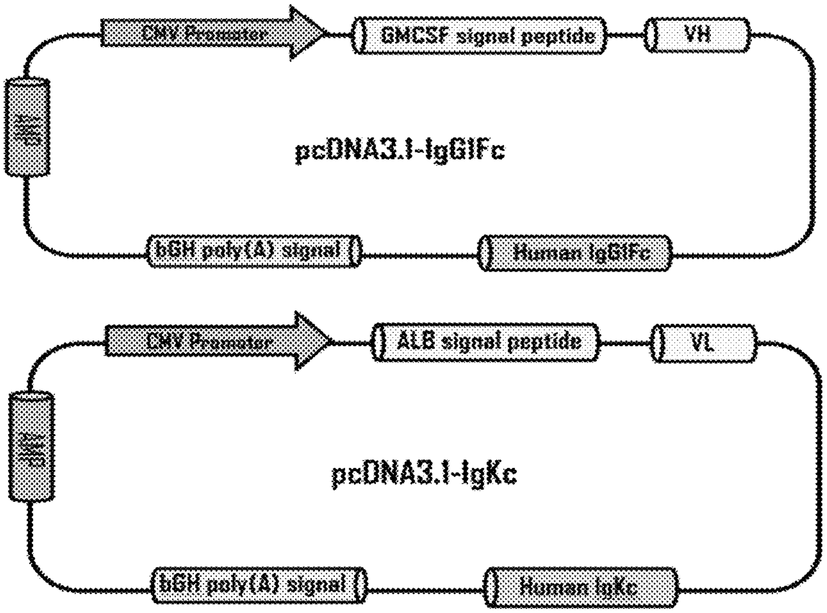
FIG. 1 shows the schematic profile of the heavy chain expression vector pcDNA3.1-IgG1Fc and the light chain expression vector pcDNA3.1-IgKc.

Through extensive and intensive research, the inventor unexpectedly discovered an antibody targeting CD276 with high affinity and specificity for the first time, and prepared humanized antibodies with affinity comparable to the chimeric antibodies. Experiments show that the antigen epitope of the antibody of the present invention is the $31^{st}$ to $40^{th}$ amino acids at the N-terminus of the CD276 protein. The antibody of the present invention binds specifically to the CD276 protein, does not bind specifically to other membrane proteins, and has excellent specificity and safety. On this basis, the present invention has been completed.

Terms

As used herein, the terms "administration" and "treatment" refer to the application of exogenous drugs, therapeutic agents, diagnostic agents or compositions to animals, humans, subjects, cells, tissues, organs or biological fluids. "Administration" and "treatment" can refer to treatment, pharmacokinetics, diagnosis, research and experimental methods. The treatment of cells includes contacting the reagents with cells, contacting the reagents with fluids, and contacting the fluids with cells. "Administration" and "treatment" also refer to treatment by reagents, diagnostics, binding compositions, or by another cells in vitro and ex vivo. When "treatment" is applied to humans, animals or research subjects, it refers to treatment, prevention or preventive measures, research and diagnosis, including contacting the anti-CD276 antibodies with humans or animals, subjects, cells, tissues, physiological compartments or physiological fluids.

As used herein, the term "treatment" refers to the administration of an internal or external therapeutic agent, including any one of the anti-CD276 antibodies and compositions of the present invention, to a patient who has one or more disease symptoms, wherein the therapeutic agent is known to have a therapeutic effect on these symptoms. Usually, the therapeutic agent is administered to a patient with an amount effective to alleviate one or more disease symptoms (a therapeutically effective amount).

As used herein, the term "optional" or "optionally" means that the event or situation described thereafter may occur, but not necessarily. For example, "optionally comprises 1-3 antibody heavy chain variable regions" means that the antibody heavy chain variable region of a specific sequence may be comprised but does not have to be comprised, and number can be 1, 2 or 3.

Antibody

As used herein, the term "antibody" refers to an immunoglobulin, which is a tetrapeptide chain structure formed by two identical heavy chains and two identical light chains connected by interchain disulfide bonds. The immunoglobulin heavy chain constant regions have different amino acid compositions and arrangements, so that their antigenicities are also different. According to this, immunoglobulins can be divided into five categories, or called different types of immunoglobulins, namely IgM, IgD, IgG, IgA and IgE, and the heavy chain constant regions corresponding to the different types of immunoglobulins are called α, δ, ε, γ, and μ, respectively. IgG represents the most important class of immunoglobulins. Due to differences in chemical structure and biological functions, it can be divided into 4 subclasses: IgG1, IgG2, IgG3, and IgG4. The light chain is divided into κ or λ chain, chains by different constant regions. The subunit structures and three-dimensional configurations of different classes of immunoglobulins are well known to those skilled in the art.

The sequence of about 110 amino acids near the N-terminus of the antibody heavy and light chains varies greatly and are variable regions (V regions); the remaining amino acid sequences near the C-terminus are relatively stable and are constant regions (C regions). The variable region includes three hypervariable regions (HVR) and four relatively conserved FR regions (FR). The amino acid sequences of the four FRs are relatively conservative and do not directly participate in the binding reaction. The three hypervariable regions determine the specificity of the antibody, also known as the complementarity determining regions (CDR). Each light chain variable region (LCVR) and heavy chain variable region (HCVR) are composed of 3 CDR regions and 4 FR regions, and the sequence from the amino terminal to the carboxy terminal is FR1, CDR1, FR2, CDR2, FR3, CDR3, FR4. The three CDR regions of the light chain, namely light chain hypervariable regions (LCDR), refer to LCDR1, LCDR2, and LCDR3; and the three CDR regions of the heavy chain, namely heavy chain hypervariable regions (HCDR), refer to HCDR1, HCDR2, and HCDR3. The number and position of the CDR amino acid residues of the LCVR and HCVR regions of the antibody or antigen-binding fragment of the present invention comply with the known Kabat numbering rules (LCDR1-3, HCDR2-3), or the numbering rules of kabat and chothia (HCDR1). The four FR regions in the natural heavy and light chain variable regions are roughly in a β-fold configuration, connected by the three CDRs that form a connecting loop, and in some cases form a part of the β-folded structure. The CDRs in each chain are closely together through the FR region and form the antigen-binding site of the antibody together with the CDRs of the other chain. The amino acid sequences of antibodies of the same type can be compared to determine which amino acids constitute the FR or CDR regions. The constant regions are not directly involved in the binding of antibodies to antigens, but they exhibit different effector functions, such as participation in the antibody-dependent cytotoxicity of antibodies.

As used herein, the term "antigen binding fragment" refers to a Fab fragment, a Fab' fragment, a F (ab')2 fragment, or a single Fv fragment that has antigen-binding activity. An Fv antibody comprises a heavy chain variable region and a light chain variable region, but does not comprise a constant region, and is the smallest antibody fragment with all antigen binding sites. Generally, an Fv antibody also comprises a polypeptide linker between the VH and VL domain, and can form the structure required for antigen binding.

As used herein, the term "antigen determinant" refers to a discrete three-dimensional site on an antigen that is recognized by the antibody or antigen-binding fragment of the present invention.

The present invention includes not only intact antibodies, but also immunologically active fragments of antibody fragments or fusion proteins formed by antibodies and other sequences. Therefore, the present invention also includes fragments, derivatives and analogs of the antibodies.

In the present invention, antibodies include murine, chimeric, humanized, or fully human antibodies prepared by techniques well known to those skilled in the art.

Recombinant antibodies, such as chimeric and humanized monoclonal antibodies, including human and non-human parts, can be prepared using DNA recombinant techniques well known in the art.

As used herein, the term "monoclonal antibody" refers to an antibody secreted by a clone derived from a single cell. Monoclonal antibodies are highly specific and direct against a single epitope. The cells may be eukaryotic, prokaryotic or phage cloned cell lines.

As used herein, the term "chimeric antibody" is an antibody molecule expressed by splicing the V region gene of a murine antibody and the C region gene of a human antibody into a chimeric gene, and then inserting the chimeric gene into a vector to transfect a host cell. It not only retains the high specificity and affinity of parental mouse antibody, but also enables its human-derived Fc segment to effectively mediate the biological effector functions.

As used herein, the term "humanized antibody" is a variable region modification form of the murine antibody of the present application. It has CDRs derived from (or substantially derived from) a non-human antibody (e.g., which may be a mouse monoclonal antibody), and FRs and constant regions substantially derived from the human antibody sequence. That is, the CDR sequences of the murine antibody are grafted onto different types of human germline antibody framework sequences. Since the CDR sequences are responsible for most of the antibody-antigen interactions, recombinant antibodies that mimic specific naturally occurring antibody properties can be expressed by constructing expression vectors.

In the present invention, the antibody may be monospecific, bispecific, trispecific, or multispecific.

In the present invention, the antibody of the present invention also includes conservative variants thereof, which means that compared with the amino acid sequence of the antibody of the present invention, there are at most 10, preferably at most 8, more preferably at most 5, most preferably at most 3 amino acids replaced by amino acids with the same or similar properties to form a polypeptide. These conservatively variant polypeptides are preferably produced by amino acid substitution according to Table A.

TABLE A

| Initial residue | Representative substitution | Preferred substitution |
|---|---|---|
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

Anti-CD276 Antibody

As used herein, the term "CD276" generally refers to natural or recombinant human CD276, as well as non-human homologues of human CD276.

The present invention provides an antibody targeting CD276 with high specificity and high affinity, which comprises a heavy chain and a light chain, wherein the heavy chain comprises a heavy chain variable region (VH) amino acid sequence, and the light chain comprises a light chain variable region (VL) amino acid sequence.

Preferably, the CDR of the heavy-chain variable region (VH) is selected from the group consisting of:

a CDR1 set forth in SEQ ID NO: 1, a CDR2 set forth in SEQ ID NO: 2, and a CDR3 set forth in SEQ ID NO: 3 or 7; and/or the CDR of the light-chain variable region (VL) is selected from the group consisting of:

a CDR1' set forth in SEQ ID NO: 4, a CDR2' set forth in SEQ ID NO: 5, and a CDR3' set forth in SEQ ID NO: 6.

Among them, any of the above amino acid sequences further includes a derivative sequence which has been added, deleted, modified and/or substituted with at least one (such as 1-5, 1-3, preferably 1-2, and more preferably 1) amino acid and has binding affinity to CD276.

In another preferred embodiment, the sequence formed by adding, deleting, modifying, and/or substituting at least one amino acid has preferably at least 80% amino acid sequence homology, more preferably at least 85%, more preferably at least 90%, and the most preferably at least 95%.

The antibody of the present invention can be a double stranded or a single stranded antibody, and can be selected from an animal derived antibody, a chimeric antibody, and a humanized antibody, more preferably a humanized antibody, a human-animal chimeric antibody, and more preferably a fully humanized antibody.

The antibody derivative described in the present invention can be a single chain antibody, and/or an antibody fragment, such as Fab, Fab', $(Fab')_2$ or other known antibody derivatives in the field, as well as any one or more of IgA, IgD, IgE, IgG, and IgM antibodies or other subtypes of antibodies.

Among them, the animal is preferably a mammal, such as a mouse.

The antibody of the present invention may be a murine antibody, chimeric antibody, humanized antibody, or CDR-grafted and/or -modified antibody targeting human CD276.

Preparation of the Antibody

Any method suitable for producing monoclonal antibodies can be used to produce the anti-CD276 antibodies of the present invention. For example, an animal can be immunized with CD276 or a fragment thereof. Suitable immunization methods can be used, including adjuvants, immunostimulants, repeated booster immunizations, and one or more approaches can be used.

Any suitable form of CD276 (e.g. a CHO-K1-CD276 recombinant cell strain) can be used as an immunogen (antigen) to produce non-human antibodies specific for CD276 and to screen the biological activity of the antibody. The stimulatory immunogen can be a full-length mature human CD276 which includes a natural homodimer, or a peptide containing single/multiple epitopes. The immunogen can be used alone or in combination with one or more immunogenicity enhancers known in the art. The immunogen can be purified from natural sources or produced in genetically modified cells. DNA encoding an immunogen may be of genomic origin or non-genomic origin (e.g. cDNA). Appropriate genetic vectors can be used to express the DNA encoding the immunogen, including but not limited to adenovirus vectors, adeno-associated virus vectors, baculovirus vectors, plasmids and non-viral vectors.

Humanized antibodies can be selected from any kind of immunoglobulin, including IgM, IgD, IgG, IgA and IgE. In the present invention, the antibody is an IgG antibody and employs IgG1 subtype. With the biological assays described in the examples below to screen antibodies, it is easy to optimize the essential constant domain sequence, so as to produce the desired bioactivity.

Likewise, any type of light chain can be used in the compounds and methods herein. Specifically, the kappa, lambda chains or variants thereof can be used in the compounds and methods of the present invention.

The sequence of the DNA molecule for the antibody or a fragment thereof according to the present invention can be obtained by conventional techniques, for example, methods such as PCR amplification or genomic library screening. In addition, the sequences encoding light chain and heavy chain can be fused together, to form a single-chain antibody.

Once a relevant sequence is obtained, recombination methods can be used to obtain the relevant sequence in large quantities. This is usually carried out by cloning the sequence into a vector, transforming a cell with the vector, and then separating the relevant sequence from the proliferated host cell by conventional methods.

In addition, a relevant sequence can be synthesized artificially, especially when the fragment is short in length. Usually, several small fragments are synthesized first, and then are linked together to obtain a fragment with a long sequence. Then, the DNA sequence can be introduced into various existing DNA molecules (or, for example, vectors) and cells known in the art.

The present invention further relates to a vector comprising said suitable DNA sequence and a suitable promoter or a control sequence. These vectors can be used to transform suitable host cells to enable them to express protein.

The host cell can be a prokaryotic cell, such as a bacterial cell; or a lower eukaryotic cell, such as a yeast cell; or a higher eukaryotic cell, such as an animal cell. Preferred animal cells comprise, but are not limited to, CHO-S, CHO-K1, HEK-293 cells.

The step of transforming host cells with recombinant DNA as described in the present invention can be carried out by techniques well known in the art. The obtained transformant can be cultured by conventional methods, and the transformant expresses the polypeptide encoded by the gene of the present invention. According to the host cell used, it is cultured in a conventional medium under suitable conditions.

In general, under conditions suitable for expression of the antibody according to the present invention, the host cell obtained is cultured. Then, the antibody according to the present invention is purified by using conventional immunoglobulin purification steps, for example, the conventional separation and purification means well known to those skilled in the art, such as protein A-Sepharose, hydroxyapatite chromatography, gel electrophoresis, dialysis, ion exchange chromatography, hydrophobic chromatography, molecular sieve chromatography or affinity chromatography.

The monoclonal antibody obtained can be identified by conventional means. For example, the binding specificity of a monoclonal antibody can be determined by immunoprecipitation or an in vitro binding assay (such as radioimmunoassay (RIA) or enzyme-linked immunosorbent assay (ELISA)).

Antibody-Drug Conjugate (ADC)

The present invention also provides an antibody-drug conjugate (ADC) based on the antibody of the present invention.

Typically, the antibody-drug conjugate comprises the antibody and an effector molecule, wherein the antibody is conjugated, preferably chemically conjugated to the effector molecule. Preferably, the effector molecule is a therapeutically active drug. In addition, the effector molecule may be one or more of a toxic protein, a chemotherapeutic drug, a small-molecule drug or a radionuclide.

The antibody of present invention and the effector molecule may be coupled by a coupling agent. Examples of the coupling agent may be any one or more of a non-selective coupling agent, a coupling agent utilizing a carboxyl group, a peptide chain, and a coupling agent utilizing a disulfide bond. The non-selective coupling agent refers to a compound that forms a covalent bond between the effector molecule and the antibody, such as glutaraldehyde, etc. The coupling agent utilizing a carboxyl group may be any one or more of cis-aconitic anhydride coupling agents (such as cis-aconitic anhydride) and acyl hydrazone coupling agents (the coupling site is acyl hydrazone).

Certain residues on an antibody (such as Cys or Lys, etc.) are used to link a variety of functional groups, including imaging agents (such as chromophores and fluorophores), diagnostic agents (such as MRI contrast agents and radioisotopes), stabilizers (such as poly(ethylene glycol)) and therapeutic agents. An antibody can be conjugated to a functional agent to form a conjugate of the antibody-functional agent. A functional agent (e.g., a drug, a detection reagent, a stabilizer) is conjugated (covalently linked) to an antibody. A functional agent can be linked to an antibody either directly or indirectly via a linker.

Antibodies can be conjugated to drugs to form antibody-drug conjugates (ADCs). Typically, an ADC comprises a linker between a drug and an antibody. The linker can be a degradable or non-degradable linker. Typically, the degradable linker is easily degraded in an intracellular environment, for example, the linker is degraded at the target site, thereby releasing the drug from the antibody. Suitable degradable linkers include, for example, enzyme-degradable linkers, including peptidyl-containing linkers that can be degraded by protease (e.g., lysosomal protease or endosomal protease) in a cell, or sugar linkers, for example, glucuronide-containing linkers that can be degraded by glucuronidase. Peptidyl linkers may include, for example, dipeptides, such as valine-citrulline, phenylalanine-lysine or valine-alanine. Other suitable degradable linkers include, for example, pH sensitive linkers (e.g., linkers that are hydrolyzed at a pH of below 5.5, such as hydrazone linkers) and linkers that are degraded under reducing conditions (e.g., disulfide-bond linkers). A non-degradable linker typically releases a drug under conditions that the antibody is hydrolyzed by protease.

Prior to linking to an antibody, a linker has a reactive group capable of reacting with certain amino acid residues, and the linkage is achieved by the reactive group. A thiol-specific reactive group is preferred, and includes, for example, a maleimide compound, a halogenated (e.g., iodo-, bromo- or chloro-substituted) amide; a halogenated (e.g., iodo-, bromo- or chloro-substituted) ester; a halogenated (e.g., iodo-, bromo- or chloro-substituted) methyl ketone, a benzyl halide (e.g., iodide, bromide or chloride); vinyl sulfone, pyridyl disulfide; a mercury derivative such as 3,6-di-(mercurymethyl)dioxane, wherein the counter ion is an acetate, a chloride, or a nitrate; and polymethylene dimethyl sulfide thiosulfonate. The linker may include, for example, a maleimide linked to an antibody via thiosuccimide.

A drug may be any cytotoxic, cytostatic or immunosuppressive drug. In an embodiment, an antibody is linked to a drug via a linker, and the drug has a functional group that can form a bond with the linker. For example, a drug may have an amino group, a carboxyl group, a thiol group, a hydroxyl group, or a ketone group that can form a bond with a linker. When a drug is directly linked to a linker, the drug has a reactive group before being linked to an antibody.

Useful drugs include, for example, anti-tubulin drugs, DNA minor groove binding agents, DNA replication inhibitors, alkylating agents, antibiotics, folic acid antagonists, antimetabolites, chemotherapy sensitizers, topoisomerase inhibitors, *vinca* alkaloids, etc. In the present invention, a drug-linker can be used to form an ADC in a simple step. In other embodiments, a bifunctional linker compound can be used to form an ADC in a two-step or multi-step process. For example, a cysteine residue is reacted with the reactive moiety of a linker in a first step, and then the functional group on the linker is reacted with a drug in the subsequent step, so as to form an ADC.

In general, the functional group on a linker is selected so that it can specifically react with the suitable reactive group on a drug moiety. As a non-limiting example, an azide-based moiety can be used to specifically react with the reactive alkynyl group on a drug moiety. The drug is covalently bound to the linker by 1,3-dipolar cycloaddition between the azide and alkynyl group. Other useful functional groups include, for example, ketones and aldehydes (suitable for reacting with hydrazides and alkoxyamines), phosphines (suitable for reacting with azides); isocyanates and isothiocyanates (suitable for reacting with amines and alcohols); and activated esters, for example, N-hydroxysuccinimide esters (suitable for reacting with amines and alcohols). These and other linkage strategies, for example, as described in Bioconjugation Technology (2nd Edition (Elsevier)), are well known to those skilled in the art. Those skilled in the art could understand that when a complementary pair of reactive functional groups are selected for a selective reaction between a drug moiety and a linker, each member of the complementary pair can be used for the linker, and can also be used for the drug.

The present invention further provides a method for preparing an ADC, which may further comprise: under conditions sufficient to form an antibody-drug conjugate (ADC), connecting an antibody to a drug-linker compound.

In certain embodiments, the method according to the present invention comprises: under conditions sufficient to form an antibody-linker conjugate, connecting an antibody to a bifunctional linker compound. In these embodiments, the method according to the present invention further comprises: under conditions that the drug moiety is sufficient to be covalently linked to the antibody via a linker, connecting the antibody-linker conjugate to the drug moiety.

In some embodiments, an antibody-drug conjugate (ADC) has a formula as follows:

$$Ab\text{-}(\text{LU-D})_p$$

wherein,

Ab is an antibody,

LU is a linker;

D is a drug;

and the subscript p is a value selected from 1 to 8.

Pharmaceutical Composition

The present invention further provides a composition. In the preferred embodiments, the composition is a pharmaceutical composition comprising the antibody, or an active fragment, a fusion protein or an ADC thereof, or a corresponding CAR-T cell, and a pharmaceutically acceptable carrier. In general, these substances may be formulated in a non-toxic, inert and pharmaceutically acceptable aqueous carrier medium, wherein the pH is generally about 5-8, preferably, pH is about 6-8, though the pH value may be varied depending on the nature of the substances to be formulated and the condition to be treated. The formulated pharmaceutical composition may be administered by conventional routes, including (but not limited to): intratumoral, intraperitoneal, intravenous, or topical administration.

The antibody of the present invention can also be used for cell therapy by expressing the nucleotide sequence in the cell. For example, the antibody is used for chimeric antigen receptor T cell immunotherapy (CAR-T) and the like.

The pharmaceutical composition according to the present invention can be directly used for binding to a CD276 protein molecule, and thus can be used for preventing and treating CD276 related diseases. In addition, other therapeutic agents can also be used at the same time.

The pharmaceutical composition according to the present invention comprises a safe and effective amount (e.g. 0.001-99 wt %, preferably 0.01-90 wt %, preferably 0.1-80 wt %) of the monoclonal antibody according to the present invention (or a conjugate thereof) and a pharmaceutically acceptable carrier or excipient. Such carriers include (but are not limited to): saline, buffers, glucose, water, glycerol, ethanol, and a combination thereof. Pharmaceutical preparations should correspond to the administration modes. The pharmaceutical composition according to the present invention can be prepared in the form of an injection, for example, by a conventional method using physiological saline or an aqueous solution containing glucose and other adjuvants. A pharmaceutical composition, for example, an injection and a solution, should be prepared under aseptic conditions. The administration amount of an active ingredient is a therapeutically effective amount, for example, about 1 μg per kilogram of body weight to about 5 mg per kilogram of body weight daily. In addition, the polypeptide according to the present invention may also be used in combination with an additional therapeutic agent.

When a pharmaceutical composition is used, a safe and effective amount of pharmaceutical composition is administered to a mammal, wherein the safe and effective amount is generally at least about 10 μg per kilogram of body weight, and in most cases, no more than about 50 mg per kilogram of body weight, preferably, the amount is from about 10 μg per kilogram of body weight to about 20 mg per kilogram of body weight. Of course, a specific amount should also depend on the factors such as administration route and physical conditions of a patient, which fall into the skills of skilled physicians.

Detection Application and Kit

The antibody of the present invention can be used for detection, for example, for detection of samples to provide diagnostic information.

In the present invention, the specimens (samples) used include cells, tissue samples and biopsy specimens. The term "biopsy" used in the present invention shall include all kinds of biopsy known to those skilled in the art. Therefore, the biopsy used in the present invention may include, for example, tissue samples prepared by endoscopic methods or organ puncture or needle biopsy.

The samples used in the present invention include fixed or preserved cells or tissue samples.

The present invention also provides a kit containing the antibody (or a fragment thereof) of the present invention. In a preferred embodiment of the present invention, the kit further includes a container, instructions for use, buffer, and the like. In a preferred embodiment, the antibody of the present invention can be immobilized on a detection plate.

Main Advantages of the Present Invention Include:

(a) A new murine monoclonal antibody targeting human CD276 is developed.

(b) A humanized antibody sequence of the monoclonal antibody targeting human CD276 is developed.

(c) Compared to drugs constructed using murine antibody sequences, the bispecific antibody, or CAR-T cell, or antibody-conjugated drugs constructed using humanized antibody sequences developed in the present invention can reduce the rejection reaction of drugs in vivo and further improve therapeutic efficacy.

The invention is further illustrated below in conjunction with specific embodiments. It should be understood that the examples are not intended to limit the scope of the invention. The experimental methods in the following examples which do not specify the specific conditions are usually in accordance with conventional conditions, such as conditions described in Sambrook et al., Molecular Cloning: Laboratory Manual (New York: Cold Spring Harbor Laboratory Press, 1989), or in accordance with the conditions recommended by the manufacturer. Unless otherwise stated, percentages and parts are by weight.

General Materials and Methods:

1. Main Reagents Used in the Examples are as Follows:

PBS (Gibco, CAT #14190-250)
DMEM (Gibco, CAT #41965-062)
F12K (Gibco, CAT #21127030)
RPMI1640 (Gibco, CAT #61870044)
FBS (Gibco, CAT #10099-141)
Genomic DNA Purification Kit (Thermo, CAT #K0512)
T4 DNA Ligase (Takara, CAT #2011B)
B7-H3 (CD276) Protein, Human, Recombinant (His Tag), (Sinobiological, Cat #11188-H08H)
PrimeScript™ 1st Strand cDNA Synthesis Kit (Takara, Cat #6110A)
Trizol RNA Extraction Reagent (Thermo, CAT #15596018)
Q5 PCR Cloning Kit (NEB, Cat #E055S)
AxyPrep DNA Gel Recovery Kit (Axygen, Cat #AP-GX-250G)
BamHI Restriction Endonuclease (NEB, CAT #R3136M)
KpnI Restriction Endonuclease (NEB, CAT #R3142M)
TOP10 competent (prepared by iCarTab)
PCDNA3.1-IgG1Fc vector (prepared by iCarTab)
PcDNA3.1-IgKc vector (prepared by iCarTab)
PE-Anti-human-IgG (Biolegend, CAT #409304)
PE-Anti-mouse IgG (MultiSciences, CAT #70-GAM0041)
FreeStyle™ 293 Expression Medium (Thermo, CAT #12338018)
LVtransm Transfection Reagent (iCarTab, Cat #LVTran100)
Buffer: 10×HBS-EP (GE, LOT: BCBV2312)
Amino coupling kit (GE, LOT: 2067793)
pH 5.5 acetate buffer (GE, LOT: 20278961601)
pH 1.5 glycine buffer (GE, LOT: 10240798)
S-series CM5 chip (GE, LOT: 10255694)

2. Main Instruments Used in the Examples are as Follows:

Ordinary optical inverted microscope
Tabletop centrifuge Thermo ST41
High speed centrifuge Thermo RC6+
Biosafety cabinet
Roche480 fluorescence quantitative PCR instrument
Thermo Attune Nxt flow cytometer
Thermo 3111 $CO_2$ incubator
BiaCore T200

3. Main Methods Involved in the Examples are as Follows:

3.1 Hybridoma Screening 3.1.1 Immunization of Mice

5 Balb/c mice were prepared. The CHO-K1-CD276 recombinant cell strain was washed 5 times with normal saline, and then used for intraperitoneal injection. Each mouse were intraperitoneally injected with $5\times10^6$ recombinant cell strains once every 14 days. 10 days after the third intraperitoneal injection, 100 μL of peripheral blood was collected through the tail vein of mice for immune titer testing. Mice with the best immune titer were selected and booster-immunized by infusion of $5\times10^6$ recombinant cell strains through the tail vein. The mouse spleens were isolated for hybridoma fusion three days after immunization.

3.1.2 Immune Titer Detection

1) Mice were taken from the cage, and their tails were disinfected with 75% medical alcohol cotton balls and punctured using a 5 mm blood sampling needle to make a small wound;
2) blood droplets were collected using capillary glass blood-collecting vessels (100 uL of plasma needs to be prepared);
3) after blood collection, the blood collection site was gently pressed with a dry sterile cotton ball to stop bleeding, and then the mice were returned to the cage for observation;
4) the centrifuge tubes containing blood sample were placed in a 37° C. incubator for 1 hour; and then the blood samples were transferred to 4° C. overnight.
5) Serum was separated from the blood clot and transferred into a new sterile centrifuge tube, centrifuged at 4° C. and 10000×g for 10 minutes;
6) the serum were transferred into a new sterile centrifuge tube for immune titer detection by ELISA.

3.1.3 ELISA Detection

1) The CD276-His recombinant protein was diluted with sterile PBS to a final concentration of 1 ug/mL. A new 96 well plate was taken and coated with 100 uL/well of protein at 4° C. overnight.
2) The antigen coating solution was discarded, and the plate was washed 3 times with PBST (containing 0.5% Tween).
3) 200 uL/well of 3% BSA was added at 37° C. for blocking for 2 hours;
4) After discarding the sealed buffer, the well plate was washed 3 times with PBST;
5) 100 ul of hybridoma supernatant was added and incubated at room temperature for 1 hour, and PBS was used as the control well;
6) solution in the wells were discarded, and the well plate was washed 3 times with PBST;
7) 100 ul of HRP-mouse IgG (diluted at 1:10000) was added, and incubated at room temperature for 1 hour;
8) solution in the wells were discarded, and the well plate was washed 3 times with PBST;
9) 100 uL/well of TMB developing solution was added;
10) The plate was incubated at room temperature in dark for 15 minutes;
11) 50 uL/well of stopping solution was added; and
12) a microplate reader was used to read the O.D value of the wells.

3.1.4 Hybridoma Fusion

1) Mice with the best immune titer were sacrificed by cervical dislocation, and their spleens were obtained in a sterile environment. B cell single cell suspension was prepared and mixed with non-antibody secreting SP2/0 myeloma cells in a ratio of 1:1, and cell fusion was performed by using a Bio-rad Gene Pulser electroporation system.
2) After electrofusion, all cells were immediately suspended in complete culture medium (DMEM, 20% FBS and HAT) and seeded into a 96 well plate.
3) After 10 days of fusion, the medium was replaced with HT culture medium. After two days of culture, the supernatant was taken for detection of the specific antibody.

3.1.5 Hybridoma Screening

120 μL of culture medium supernatant was taken from each well of the 96 well plate, and fresh HT culture medium was added to each well. The taken culture medium was incubated with an ELISA well plate pre-coated with the target antigen, and was identified according to a standard ELISA operation step. Wells with higher O.D values were selected for the second and third rounds of subcloning. After each round of subcloning, ELISA detection was performed according to the same steps, until the formation of a single clone.

3.1.6 Flow Cytometry Detection of Hybridoma Clones

1) K562-CD276 cell strains were thawed from liquid nitrogen and the cell state was adjusted to the logarithmic growth phase by using RPMI1640 and 10% FBS complete culture medium.
2) The K562-CD276 cell strains were divided into several parts with $5\times10^5$ cells in each part. The target cells were respectively incubated with 100 uL hybridoma supernatant, well mixed, and incubated at room temperature for 1 hour.
3) The cells were centrifuged at 800×g at room temperature for 5 minutes, the supernatant containing antibodies was discarded, and the cells were washed 3 times with PBS.
4) Then 0.5 μl of PE-labeled Anti-mouse IgG was added, mixed well, and incubated at room temperature in dark place for 30 min.
5) The cells were centrifuged at 800×g at room temperature for 5 minutes, the supernatant containing the secondary antibodies was discarded, and the cells were washed 3 times with PBS.
6) The cells were resuspended in 500 μL of PBS, and then subjected to the flow cytometry.

3.2 Hybridoma Screening $5\times10^6$ final screened hybridoma cells were taken, lysed with Trizol, and the total RNA of the hybridoma cells was extracted according to standard methods.

After reverse transcription of the total RNA into cDNA sample by using a reverse transcription kit, the heavy chain and light chain variable regions of the antibodies were amplified by using hybridoma sequencing primers through PCR. Then TA cloning was performed by subcloning the fragments obtained by PCR into pMD-19T vectors. After blue-white selection, 10 clones of each chain were picked respectively for sequencing. The finally obtained antibody sequences were analyzed.

3.3 Humanization of Murine Antibody 3.3.1 Design of Humanized Antibody Sequence

Humanization design was performed according to the amino acid sequence information of the heavy chain and the light chain of the target antibody obtained by the above mentioned sequencing. The CDR region sequences of the original antibody remained unchanged, and different humanized antibody templates were selected for the heavy chain and light chain respectively, according to the results of the germline alignment and the results of antibody structure simulation, then reverse mutations were carried out in the humanized frame region, in order to design candidate humanized antibody sequences.

3.3.2 Synthesis of Humanized Antibody Gene and Construction of Expression Vector The heavy and light chains of the humanized antibody designed above were subjected to gene synthesis, and the heavy chain was subcloned into the pcDNA3.1-IgG1Fc expression vector, while the light chain was subcloned into the pcDNA3. 1-IgKc expression vector (the vector profiles are shown in FIG. 1). After the vectors were sequenced and confirmed to be correct, endotoxin free plasmids were prepared by using Qiagen plasmid extraction kit.

3.3.3 Expression and Purification of Humanized Antibody

1) LVTransm transfection reagent and antibody expression vectors were taken from the refrigerator, thawed at room temperature, and then blown up and down with a pipette until well mixed. PBS or HBSS buffer was taken out and warmed to room temperature. 2 mL of PBS was taken into one hole of the 6-well plate and added with 2 μg pcDNA3.1-IgG1Fc and 2 μg pcDNA3.1-IgKc, blown up and down with a pipette until well mixed, then added with 12 μL of LVTransm and immediately blown up and down with a pipette until well mixed, then it was placed at room temperature for 10 minutes.
2) The above DNA/LVTransm complex was added into 1.5 mL of 293F-SVP16 cells, gently shaken until well mixed. The cells were placed in a 37° C., 5% $CO_2$ incubator and cultured at 130 RPM for 6-8 hours. Then 1.5 mL of fresh FreeStyle™ 293 expression culture medium was added, and the cells were returned to the incubator for further cultivation.
3) After 3 days of continuous culture, the culture supernatant was collected and filtered with a filter membrane of 0.45 μm, and the filtrate was transferred to a sterile centrifuge tube for flow cytometry detection.

3.3.4 Identification of the Binding of Humanized Antibody to Target Protein by Flow Cytometry 1) CHO-K1 empty cells and CHO-K1-CD276 recombinant cell strains were thawed from liquid nitrogen and the cell state was adjusted to the logarithmic growth phase by using F12K and 10% FBS complete culture medium.

2) The two cell strains were respectively divided into several parts with $5\times10^5$ cells in each part, added respectively with humanized antibodies, and each antibody was incubated with both CHO-K1 empty cell and CHO-K1-CD276 recombinant cell strain. After mixed well, the cells were incubated at room temperature for 1 hour.

3) The cells were centrifuged at 800×g at room temperature for 5 minutes, the supernatant containing antibodies was discarded, and the cells were washed 3 times with PBS.

4) 2 μl of PE-labeled Anti-Human IgG was added, mixed well, and incubated at room temperature in dark for 30 min.

5) The cells were centrifuged at 800×g at room temperature for 5 minutes, the supernatant containing the secondary antibodies was discarded, and the cells were washed 3 times with PBS.

6) The cells were resuspended in 500 μL of PBS, and then subjected to the flow cytometry.

3.3.5 Affinity Detection of Humanized Antibody

The binding capacity of the non-humanized and humanized antibodies to the target protein CD276 was detected by fixing the CD276-His recombinant protein on a CM5 chip by using a 10 mM acetic acid coupling buffer and using the above prepared positive humanized antibodies identified by flow cytometry and human-murine chimeric antibodies as the mobile phase.

Example 1 ELISA Detection of Mice Immune Titer

Figure 2:
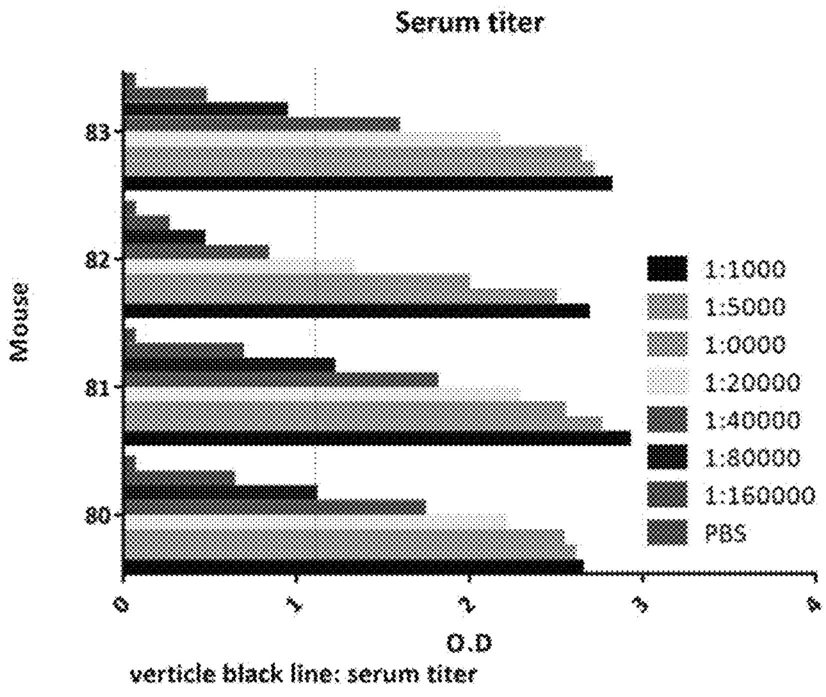
FIG. 2 shows the ELISA detection results of immunized mice.

Mice were immunized according to the above method, serum was isolated from the tail veins of all immunized mice, and limitedly diluted according to the dilution gradient shown in FIG. 2, and respectively subjected to ELISA detection on a 96 well plate pre-coated with antigens.

The results are shown in FIG. 2. Based on the experimental results, mouse No. 81 was selected for booster-immunization and subsequent hybridoma fusion.

Example 2 ELISA Detection on Fusion Plate

100 μL of supernatant from the well plate of fused hybridoma was taken for ELISA detection using a 96 well plate pre-coated with the target antigen.

Figure 3:
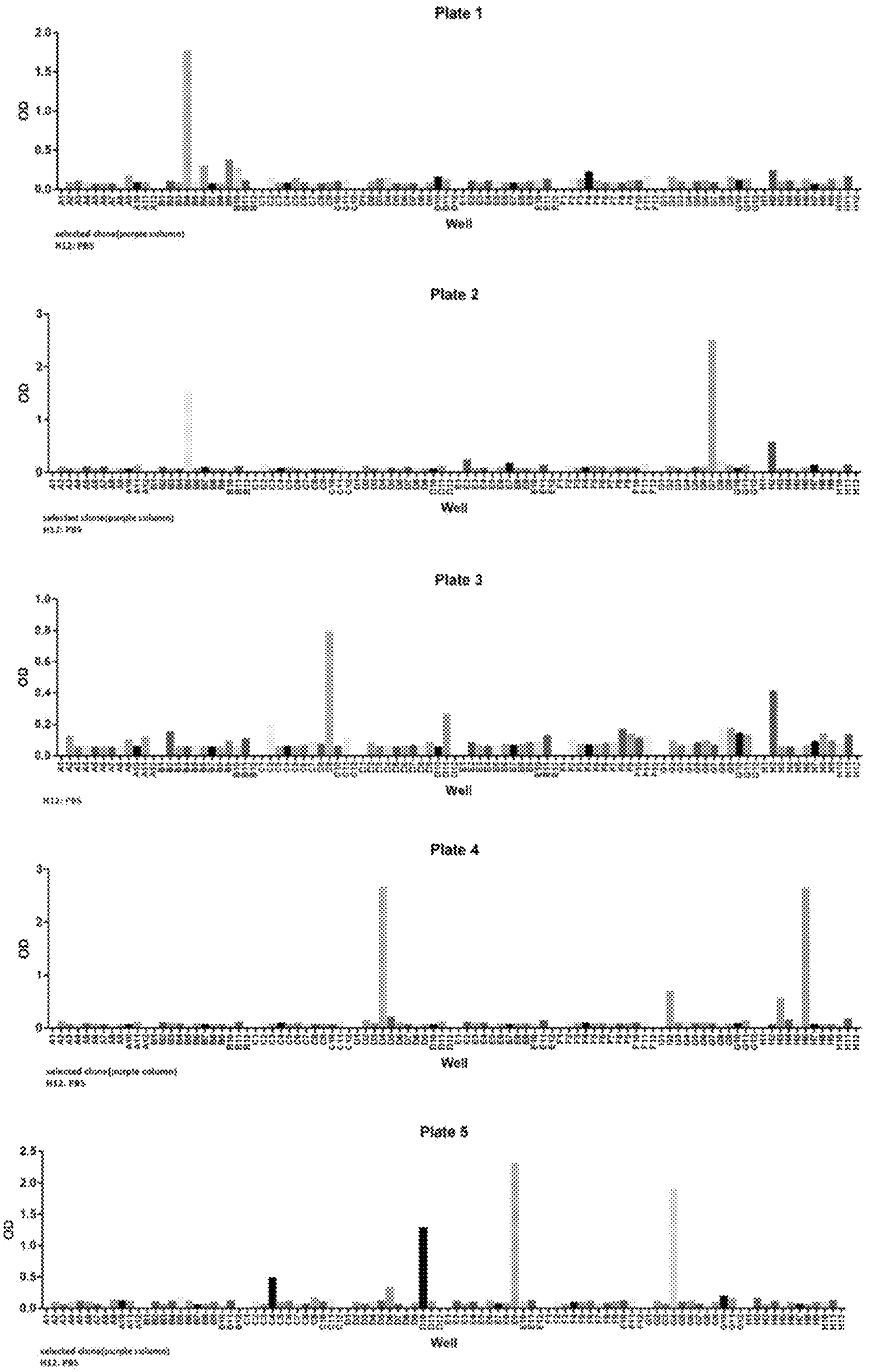
FIG. 3 shows the ELISA detection results of the hybridoma fusion plate.
Figure 3:
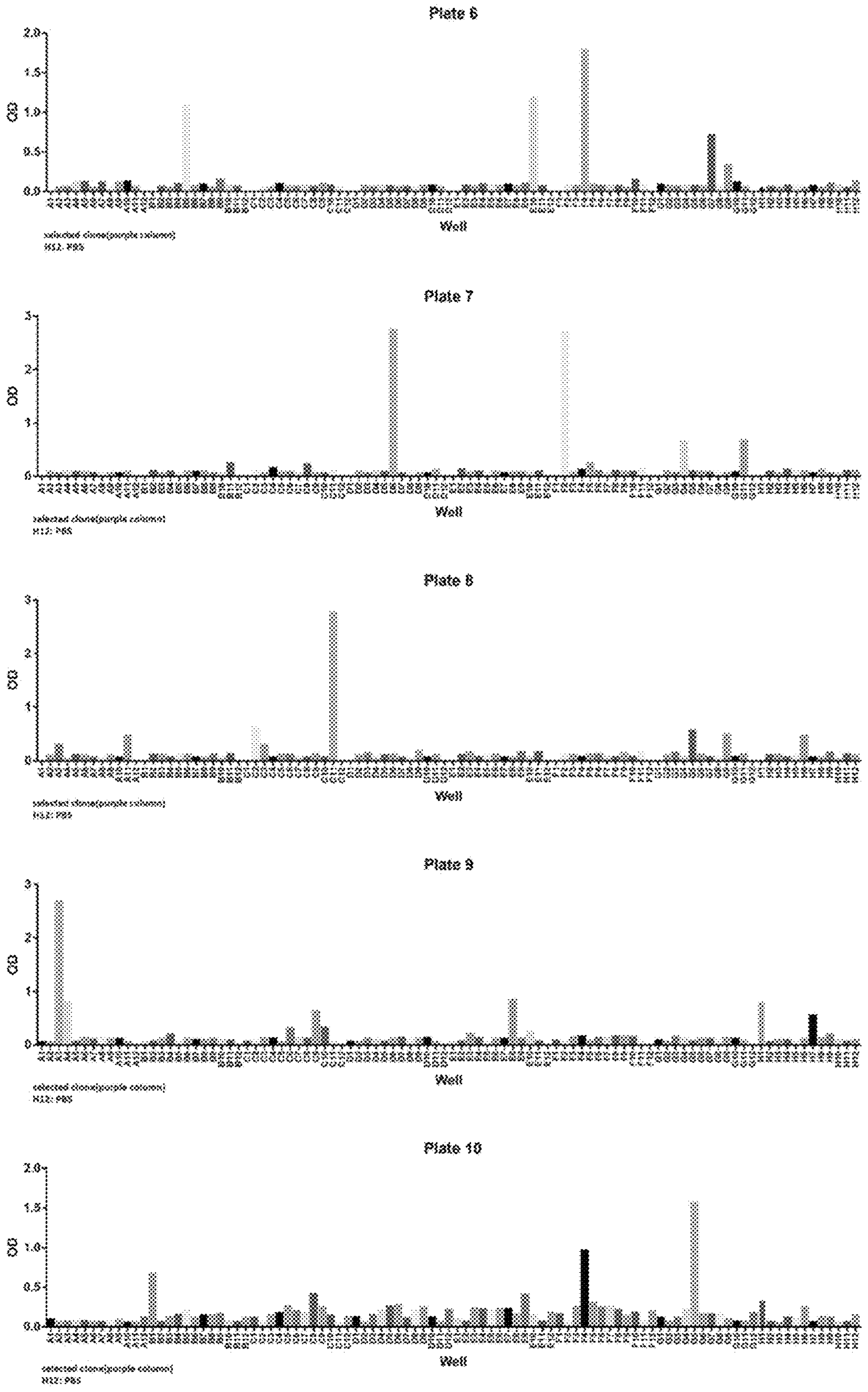

The ELISA detection results of each hybridoma fusion plate are shown in FIG. 3.

Based on the OD value of ELISA detection, the best clones were selected for the next round of subcloning. The specific clones selected include B4 of plate 1, D4 of plate 4, E9 of plate 5, F4 of plate 6, C11 of plate 8, and G5 of plate 10.

Example 3 First Subcloning

100 μL of supernatant from the well plate of first cloning was taken for ELISA detection using a 96 well plate pre-coated with the target antigen.

Figure 4:
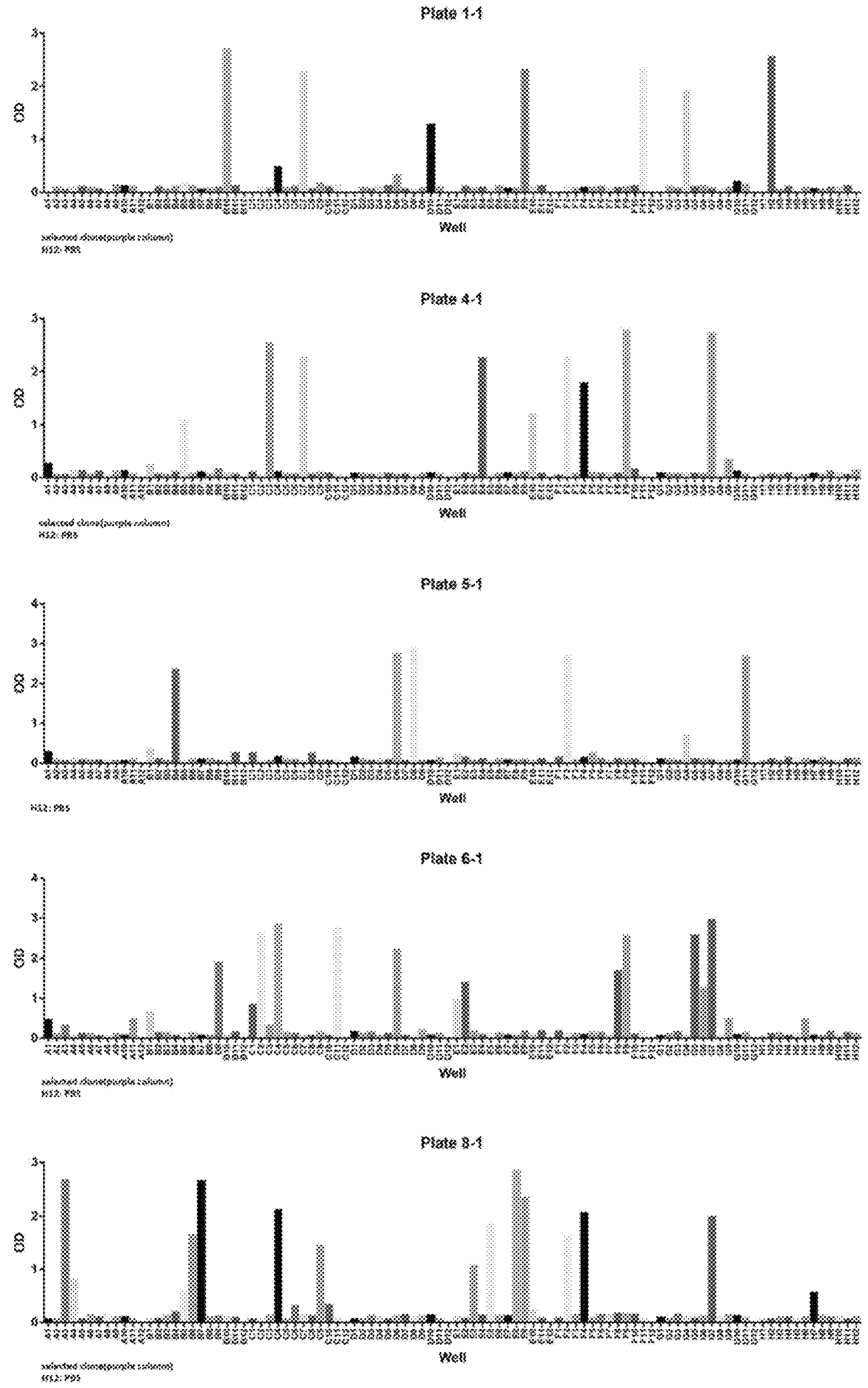
FIG. 4 shows the ELISA detection results of the first subcloning plates.
Figure 4:
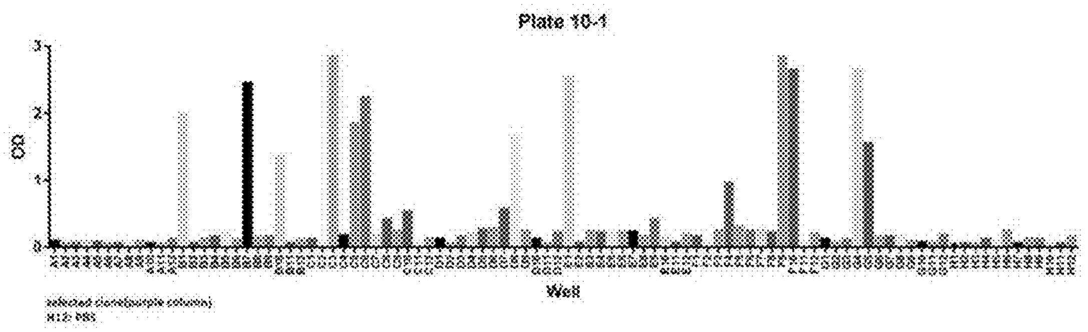

The ELISA detection results of the first subcloning are shown in FIG. 4, wherein plate 1-1 corresponds to the first subcloning result of plate 1 B4 in Example 1, plate 4-1 corresponds to the first subcloning result of plate 4 D4 in Example 1, and the remaining markers are named in a similar manner.

Based on the ELISA detection results of the first subcloning, clones with higher OD values and good growth were selected for FACS validation with K562-CD276 cell strain and the second subcloning.

Figure 5:
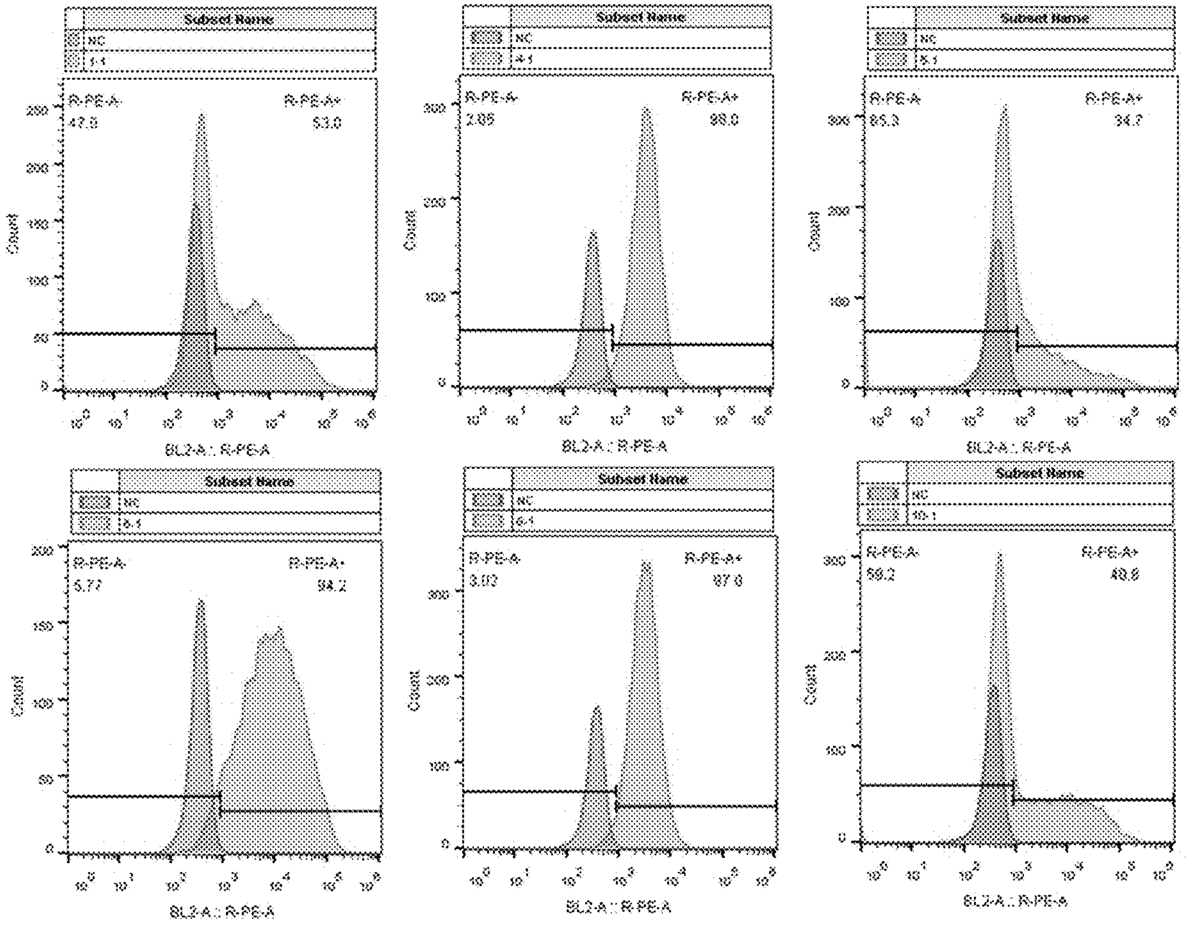
FIG. 5 shows the FACS detection results of the first subcloning.

The FACS detection results are shown in FIG. 5.

Example 4 Second Subcloning

Figure 6:
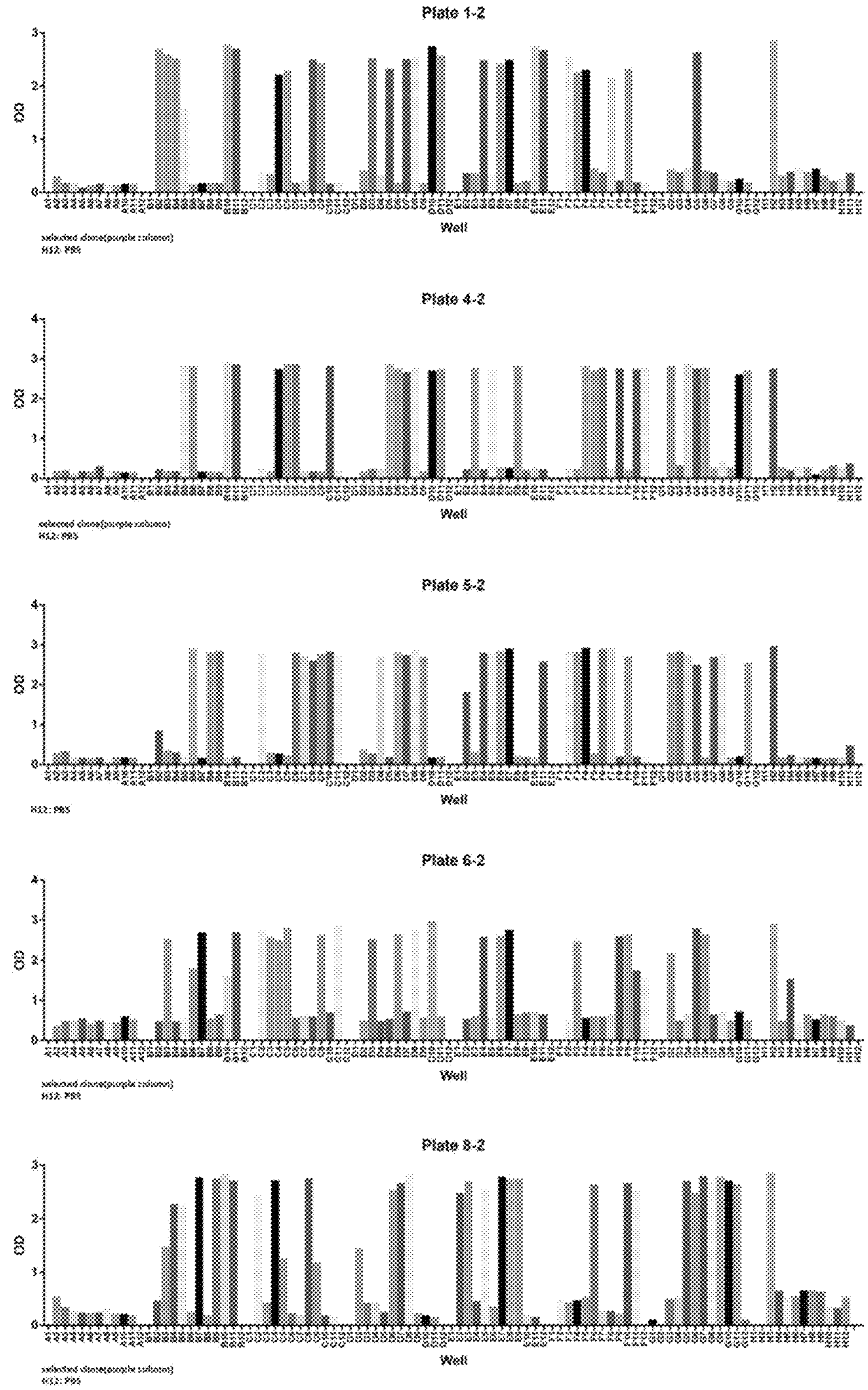
FIG. 6 shows the ELISA detection results of the second subcloning plates.
Figure 6:
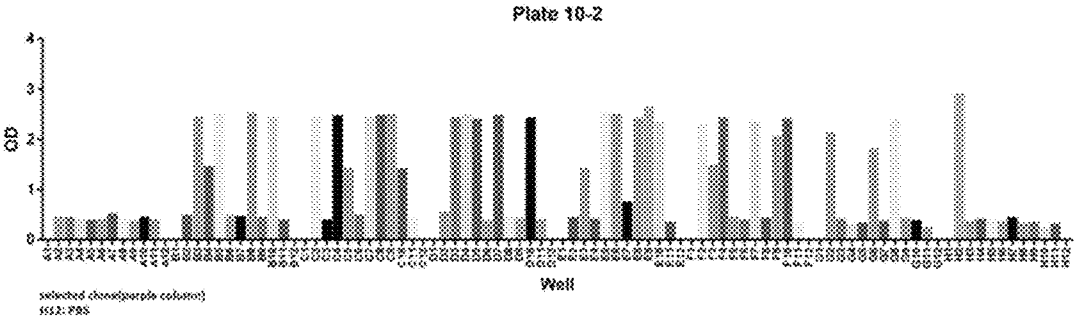

100 μL of supernatant was taken from the well plate of the second subcloning for ELISA detection using a 96 well plate pre-coated with the target antigen. The results are shown in FIG. 6, wherein plate 1-2 corresponds to the second subcloning result of plate 1 B4 in Example 1, plate 4-2 corresponds to the second subcloning result of plate 4 D4 in Example 1, and the remaining markers are named in a similar manner.

Figure 7:
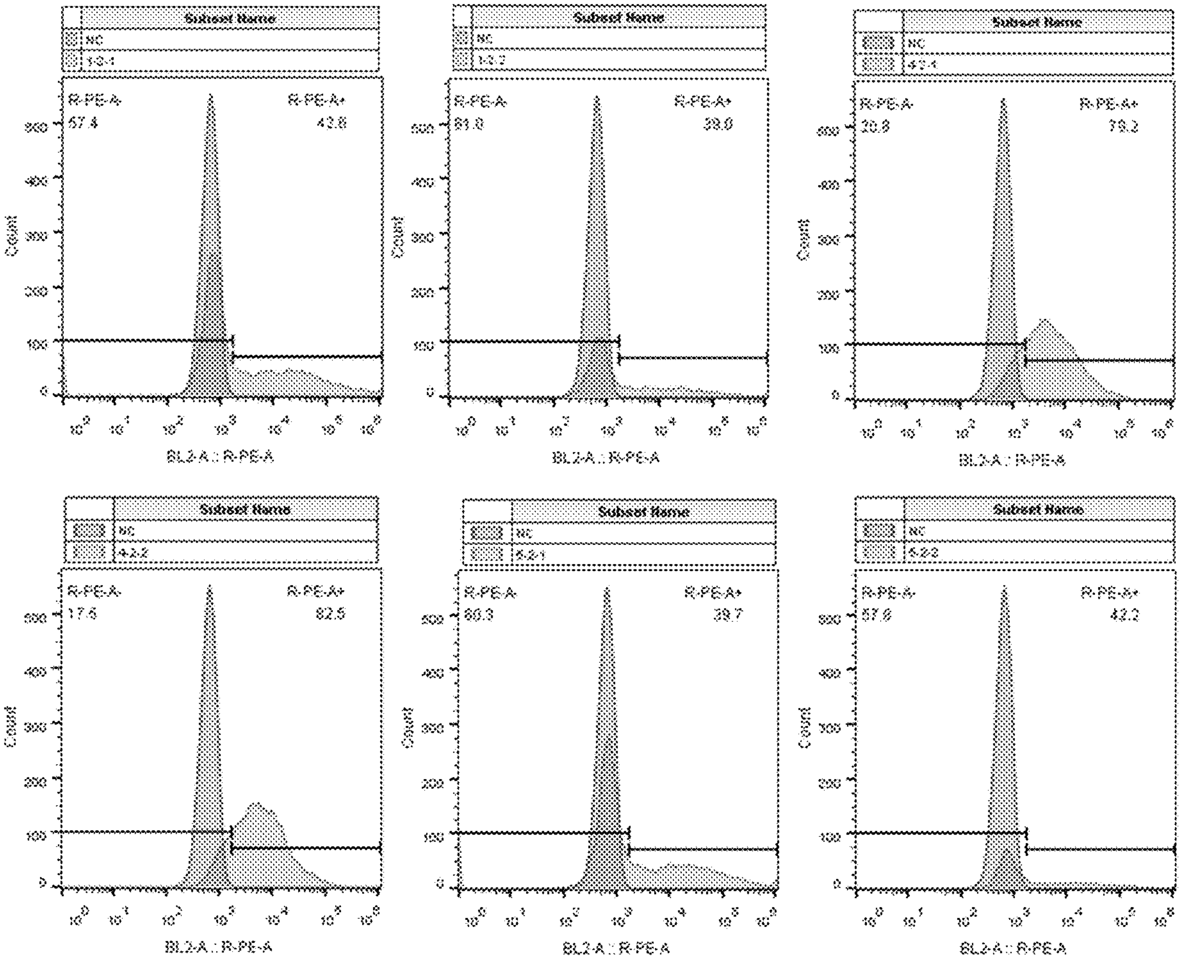
FIG. 7 shows the FACS detection results of the second subcloning.
Figure 7:
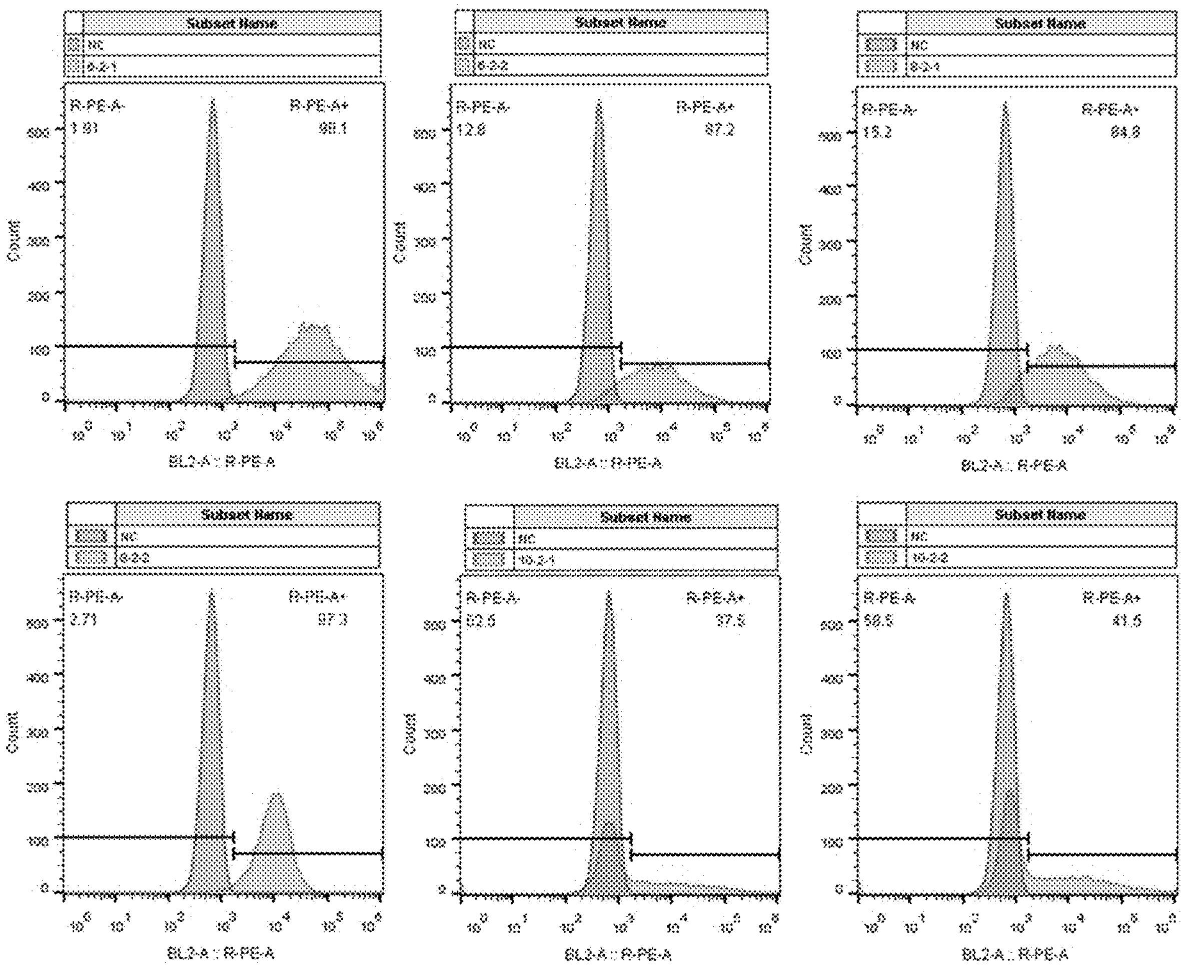

Based on the ELISA detection results of the second subcloning, clones with higher OD values and good growth were selected for FACS validation with K562-CD276 cell strain. The results are shown in FIG. 7.

Example 5 Hybridoma Sequencing

Clones with good FACS identification results were selected for amplification, and lysed with TRIZOL reagent. The RNA was extracted and reverse transcribed into cDNA. Then, the heavy and light chain variable regions corresponding to the hybridoma antibody were sequenced by using hybridoma sequencing primers, and the CDR regions and frame regions therein were analyzed. Two different heavy chain variable regions (VH, VH-7) and one light chain variable region (VL) were obtained. The specific sequences are as follows.

The amino acid sequence of the heavy chain variable region VH:
FR1-CDR1-FR2-CDR2-FR3-CDR3-FR4

```
                                              (SEQ ID NO.: 8)
EVTLVESGGGLVKPGGSLKLSCAASGFTFSTYVMSWVRQTPEKRLEWVA
SILSGGTSFYADNVKGRFTISRENARNILYLQMSSLKSEDTAMYYCVRR
YGHDRYYAMDYWGQGTSVTVSS
```

Among them, the underlined amino acid sequences are the CDR regions, which specifically includes:

```
VH CDR1:
                              (SEQ ID NO.: 1)
GFTFSTY

VH CDR2:
                              (SEQ ID NO.: 2)
LSGGT

VH CDR3:
                              (SEQ ID NO.: 7)
RYGHDRYYAMDY
```

The amino acid sequence of the heavy chain variable region VL-7:
FR1-CDR1-FR2-CDR2-FR3-CDR3-FR4

(SEQ ID NO.: 9)
EVTLVESGGGLVKPGGSLKLSCAASGFTFSTYVMSWVRQTPEKRLEWVA
SILSGGTSFYADNVKGRFTISRENARNILYLQMSSLKSEDTAMYYCVRR
YGHDHYYAMDYWGQGTSVTVSS

Among them, the underlined amino acid sequences are the CDR regions, which specifically includes:

VH-7 CDR1:
(SEQ ID NO.: 1)
GFTFSTY

VH-7 CDR2:
(SEQ ID NO.: 2)
LSGGT

VH-7 CDR3:
(SEQ ID NO.: 3)
RYGHDHYYAMDY

The amino acid sequence of the light chain variable region VL:
FR1-CDR1-FR2-CDR2-FR3-CDR3-FR4

(SEQ ID NO.: 10)
QIVLTQSPANMSASLGERVTMTCAASSSVSSSYLHWYQQKPGSSPKLWI
YSTSNLASGVPGRFNGSGSGTSYSLTISSMEAEDAATYYCHQYHRSPWT
FGGGTKLEIK

Among them, the underlined amino acid sequences are the CDR regions, which specifically includes:

VL CDR1:
(SEQ ID NO.: 4)
AASSSVSSSYLH

VL CDR2:
(SEQ ID NO.: 5)
STSNLAS

VL CDR3:
(SEQ ID NO.: 6)
QYHRSPWT

Based on the sequencing results, through the alignment of the sequences of VH-7 and VH, it is found that they only have one different amino acid in CDR3, and the specific amino acid are bolded in the sequences.

Example 6 Construction and FACS Validation of Chimeric Antibody Expression Vector Since two different heavy chain variable regions were obtained by sequencing of hybridoma, a chimeric expression vector was constructed to express antibodies for validation. The heavy chain variable region obtained from hybridoma sequencing was subcloned into the pcDNA3.1-IgG1Fc expression vector, while the light chain variable region was subcloned into the pcDNA3.1-IgKc expression vector. The constructed light chain and heavy chain expression vectors was combined in pairs and transiently co-transfected into 293F cells. After 72 hours of transfection, the expressed supernatant was collected for FACS detection.

Figure 8:
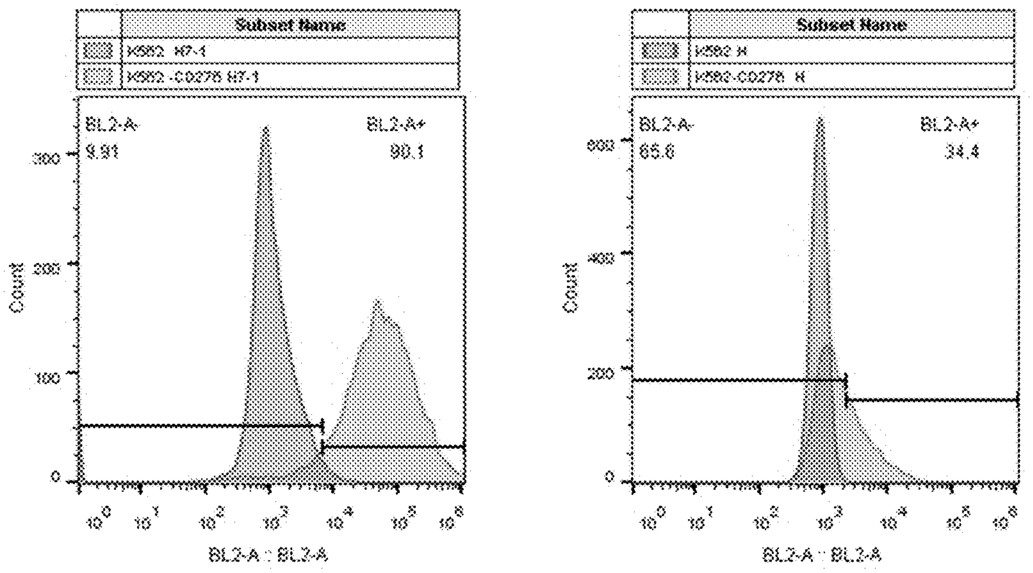
FIG. 8 shows the FACS detection results of the chimeric antibodies.

The FACS detection results are shown in FIG. 8.

Based on the flow cytometry detection results, the heavy chain variable region VH-7, shown in SEQ ID NO.: 9, and the light chain variable region VL, shown in SEQ ID NO.: 10, were determined for humanization design.

Example 7 Detection of Humanized Antibody by Flow Cytometry

A total of 5 humanized heavy chain variable regions and 5 humanized light chain variable regions were designed according to humanized antibody sequence design described in the general method.

Among them, the nucleic acid sequence information of humanized candidate antibodies are shown as follows:

>T1L1
(SEQ ID NO.: 11)
GAGATCGTGCTGACACAGTCTCCCGCCACACTGTCACTGTCTCCAGGCG
AAAGAGCCACACTGAGCTGCGCTGCCTCTAGCTCTGTGTCCAGCAGCTA
CCTGCACTGGTATCAGCAGAAGCCTGGACTGGCCCCTCGGCTGCTGATC
TACAGCACAAGCAATCTGGCCAGCGGCATCCCCGATAGATTTTCCGGCT
CTGGCTCCGGCACCGACTTCACCCTGACAATCAGCAGACTGGAACCCGA
GGACTTCGCCGTGTACTACTGCCAGCAGTACCACAGAAGCCCCTGGACA
TTTGGCGGAGGCACCAAGGTGGAAATCAAG

>T1L2
(SEQ ID NO.: 12)
GAGATCGTGCTGACACAGTCTCCCGCCACACTGTCACTGTCTCCAGGCG
AAAGAGCCACACTGAGCTGCGCTGCCTCTAGCTCTGTGTCCAGCAGCTA
CCTGCACTGGTATCAGCAGAAGCCTGGCAGCGCTCCCAGACTGCTGATC
TACAGCACAAGCAATCTGGCCAGCGGCATCCCCGATAGATTTTCCGGCT
CTGGCTCCGGCACCGACTTCACCCTGACAATCAGCAGACTGGAACCCGA
GGACTTCGCCGTGTACTACTGCCAGCAGTACCACAGAAGCCCCTGGACA
TTTGGCGGAGGCACCAAGGTGGAAATCAAG

>T1L3
(SEQ ID NO.: 13)
GAGATCGTGCTGACACAGTCTCCCGCCACACTGTCACTGTCTCCAGGCG
AAAGAGCCACACTGAGCTGCGCTGCCTCTAGCTCTGTGTCCAGCAGCTA
CCTGCACTGGTATCAGCAGAAGCCTGGCAGCGCTCCCAGACTGCTGATC
TACAGCACAAGCAATCTGGCCAGCGGCATCCCCGATAGATTTTCCGGCT
CTGGCTCCGGCACCGACTTCACCCTGACAATCTCTAGACTGGAAGCCGA
GGACTTCGCCGTGTACTACTGCCAGCAGTACCACAGAAGCCCCTGGACA
TTTGGCGGAGGCACCAAGGTGGAAATCAAG

>T2L1
(SEQ ID NO.: 14)
GACATCCAGATGACACAGAGCCCCAGCACACTGTCTGCCAGCGTGGGAG
ACAGAGTGACCATTACATGTGCCGCCAGCAGCAGCGTGTCCAGCTCTTA
CCTGCACTGGTATCAGCAGAAGCCCGGCAAGGCCCCTAAGCTGCTGATC
TACAGCACCAGCAATCTGGCCAGCGGCGTGCCAAGCAGATTTTCTGGCT
CTGGCAGCGGCACCGAGTTCACCCTGACCATCTCTAGCCTGCAGCCTGA
CGACTTCGCCACCTACTACTGCCAGCAGTACCACAGAAGCCCCTGGACA
TTTGGCCAGGGCACCAAGCTGGAAATCAAG

-continued

>T2L2

(SEQ ID NO.: 15)

GACATCCAGATGACACAGAGCCCCAGCACACTGTCTGCCAGCGTGGGAG
ACAGAGTGACCATTACATGTGCCGCCAGCAGCAGCGTGTCCAGCTCTTA
CCTGCACTGGTATCAGCAGAAGCCCGGCAAGGCCCCTAAGCTGCTGATC
TACAGCACCAGCAATCTGGCCAGCGGCGTGCCAAGCAGATTTTCTGGCT
CTGGCAGCGGCACCGAGTTCACCCTGACCATCTCTAGCCTGCAGCCTGA
TGATGCCGCCACCTACTACTGCCAGCAGTACCACAGAAGCCCCTGGACA
TTTGGCCAGGGCACCAAGCTGGAAATCAAG

>T1H1

(SEQ ID NO.: 16)

GAGGTGCAGCTGGTTGAATCTGGCGGCGGACTGATTCAGCCTGGCGGAT
CTCTGAGACTGAGCTGTGCCGCCAGCGGCTTCACCTTTAGCACCTACGT
GATGAGCTGGGTCCGACAGGCCCCTGGCAAAGGACTTGAATGGGTGTCC
AGCATCCTGAGCGGCGGCACAAGCTTCTACGCCGACAATGTGAAGGGCA
GATTCACCATCAGCCGGGACAACAGCAAGAACACCCTGTACCTGCAGAT
GAACAGCCTGAGAGCCGAGGACACCGCCGTGTACTACTGCGCCAGAAGA
TACGGCCACGACCACTACTACGCCATGGACTATTGGGGCCAGGGCACCC
TGGTTACCGTTAGCTCT

>T1H2

(SEQ ID NO.: 17)

GAGGTGCAGCTGGTTGAATCTGGCGGCGGACTGATTCAGCCTGGCGGAT
CTCTGAGACTGAGCTGTGCCGCCAGCGGCTTCACCTTTAGCACCTACGT
GATGAGCTGGGTCCGACAGACACCTGGCAAAGGCCTGGAATGGGTGTCC
AGCATTCTGAGCGGCGGCACCAGCTTCTACGCCGACAATGTGAAGGGCA
GATTCACCATCAGCCGGGACAACAGCAAGAACACCCTGTACCTGCAGAT
GAACAGCCTGAGAGCCGAGGACACCGCCGTGTACTACTGCGCCAGAAGA
TACGGCCACGACCACTACTACGCCATGGACTATTGGGGCCAGGGCACCC
TGGTTACCGTTAGCTCT

>T1H3

(SEQ ID NO.: 18)

GAGGTGCAGCTGGTTGAATCTGGCGGCGGACTGATTCAGCCTGGCGGAT
CTCTGAGACTGAGCTGTGCCGCCAGCGGCTTCACCTTTAGCACCTACGT
GATGAGCTGGGTCCGACAGACACCTGGCAAAGGCCTGGAATGGGTGTCC
AGCATTCTGAGCGGCGGCACCAGCTTCTACGCCGACAATGTGAAGGGCA
GATTCACCATCAGCCGGGACAACAGCAAGAACACCCTGTACCTGCAGAT
GAACAGCCTGAGAGCCGAGGACACCGCCATGTACTACTGCGCCAGAAGA
TACGGCCACGACCACTACTACGCCATGGATTATTGGGGCCAGGGCACCC
TGGTCACCGTTTCTTCT

>T2H1

(SEQ ID NO.: 19)

GAGGTGCAGCTGGTTGAATCTGGTGGCGGCGTTGTCAGACCTGGCGGAT
CTCTGAGACTGAGCTGTGCCGCCAGCGGCTTCACCTTTAGCACCTACGT
GATGAGCTGGGTCCGACAGGCCCCTGGCAAAGGACTTGAATGGGTGTCC
AGCATCCTGAGCGGCGGCACAAGCTTCTACGCCGACAATGTGAAGGGCA
GATTCACCATCAGCCGGGACAACGCCAAGAACAGCCTGTACCTGCAGAT
GAACTCCCTGAGAGCCGAGGACACAGCCCTGTATCACTGCGCCAGAAGA
TACGGCCACGACCACTACTACGCCATGGACTATTGGGGCCAGGGCACCA
CCGTGACAGTCTCTTCT

>T2H2

(SEQ ID NO.: 20)

GAGGTGCAGCTGGTTGAATCTGGTGGCGGCGTTGTCAGACCTGGCGGAT
CTCTGAGACTGAGCTGTGCCGCCAGCGGCTTCACCTTTAGCACCTACGT
GATGAGCTGGGTCCGACAGACACCTGGCAAAGGCCTGGAATGGGTGTCC
AGCATTCTGAGCGGCGGCACCAGCTTCTACGCCGACAATGTGAAGGGCA
GATTCACCATCAGCCGGGACAACGCCAAGAACAGCCTGTACCTGCAGAT
GAACTCCCTGAGAGCCGAGGACACAGCCCTGTATCACTGCGCCAGAAGA
TACGGCCACGACCACTACTACGCCATGGACTATTGGGGCCAGGGCACCA
CCGTGACAGTCTCTTCT

The amino acid sequence information of humanized candidate antibodies are shown as follows:

>TIL1

(SEQ ID NO.: 21)

EIVLTQSPATLSLSPGERATLSCAASSSVSSSYLHWYQQKPGLAPRLLI
YSTSNLASGIPDRFSGSGSGTDFTLTISRLEPEDFAVYYCQQYHRSPWT
FGGGTKVEIK

>T1L2

(SEQ ID NO.: 22)

EIVLTQSPATLSLSPGERATLSCAASSSVSSSYLHWYQQKPGSAPRLLI
YSTSNLASGIPDRFSGSGSGTDFTLTISRLEPEDFAVYYCQQYHRSPWT
FGGGTKVEIK

>T1L3

(SEQ ID NO.: 23)

EIVLTQSPATLSLSPGERATLSCAASSSVSSSYLHWYQQKPGSAPRLLI
YSTSNLASGIPDRFSGSGSGTDFTLTISRLEAEDFAVYYCQQYHRSPWT
FGGGTKVEIK

>T2L1

(SEQ ID NO.: 24)

DIQMTQSPSTLSASVGDRVTITCAASSSVSSSYLHWYQQKPGKAPKLLI
YSTSNLASGVPSRFSGSGSGTEFTLTISSLQPDDFATYYCQQYHRSPWT
FGQGTKLEIK

>T2L2

(SEQ ID NO.: 25)

DIQMTQSPSTLSASVGDRVTITCAASSSVSSSYLHWYQQKPGKAPKLLI
YSTSNLASGVPSRFSGSGSGTEFTLTISSLQPDDAATYYCQQYHRSPWT
FGQGTKLEIK

>T1H1

(SEQ ID NO.: 26)

EVQLVESGGGLIQPGGSLRLSCAASGFTFSTYVMSWVRQAPGKGLEWVS
SILSGGTSFYADNVKGRFTISRDNSKNTLYLQMNSLRAEDTAVYYCARR
YGHDHYYAMDYWGQGTLVTVSS

>T1H2

(SEQ ID NO.: 27)

EVQLVESGGGLIQPGGSLRLSCAASGFTFSTYVMSWVRQTPGKGLEWVS
SILSGGTSFYADNVKGRFTISRDNSKNTLYLQMNSLRAEDTAVYYCARR
YGHDHYYAMDYWGQGTLVTVSS

>T1H3

(SEQ ID NO.: 28)

EVQLVESGGGLIQPGGSLRLSCAASGFTFSTYVMSWVRQTPGKGLEWVS
SILSGGTSFYADNVKGRFTISRDNSKNTLYLQMNSLRAEDTAMYYCARR
YGHDHYYAMDYWGQGTLVTVSS

-continued

```
>T2H1
                                        (SEQ ID NO.: 29)
EVQLVESGGGVVRPGGSLRLSCAASGFTFSTYVMSWVRQAPGKGLEWVS
SILSGGTSFYADNVKGRFTISRDNAKNSLYLQMNSLRAEDTALYHCARR
YGHDHYYAMDYWGQGTTVTVSS

>T2H2
                                        (SEQ ID NO.: 30)
EVQLVESGGGVVRPGGSLRLSCAASGFTFSTYVMSWVRQTPGKGLEWVS
SILSGGTSFYADNVKGRFTISRDNAKNSLYLQMNSLRAEDTALYHCARR
YGHDHYYAMDYWGQGTTVTVSS
```

After the humanized antibody expression vector was transiently transfected into 293F cells, the culture medium supernatant was collected, and the binding between the humanized antibody and the antigen on the surface of recombinant CHO-K1-CD276 cell membrane was detected by flow cytometry. A human-mouse chimeric antibody constructed from the VH and VL original murine antibody was used as a control.

Figure 9:
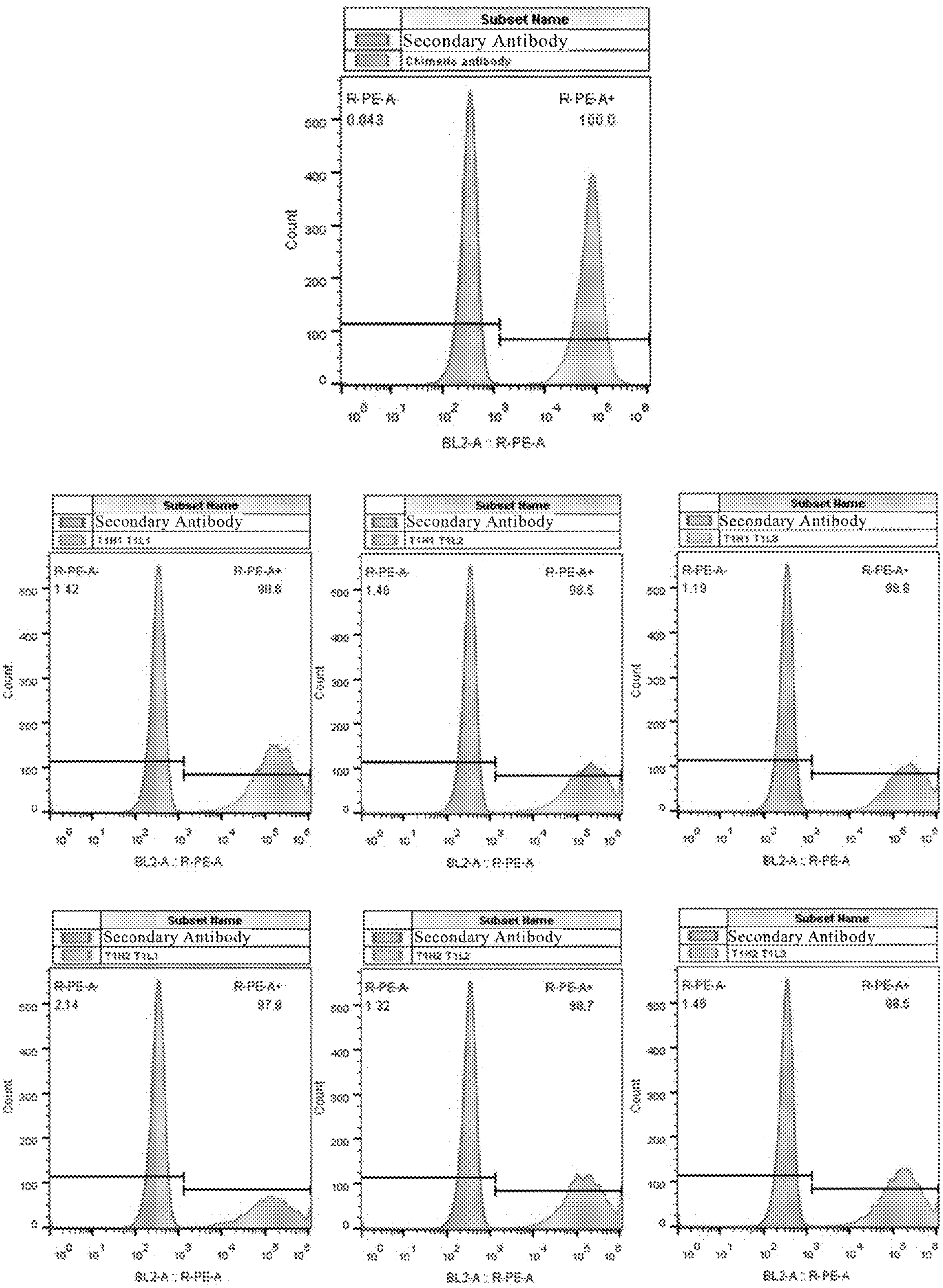
FIG. 9 shows the FACS detection results of the humanized antibodies.
Figure 9:
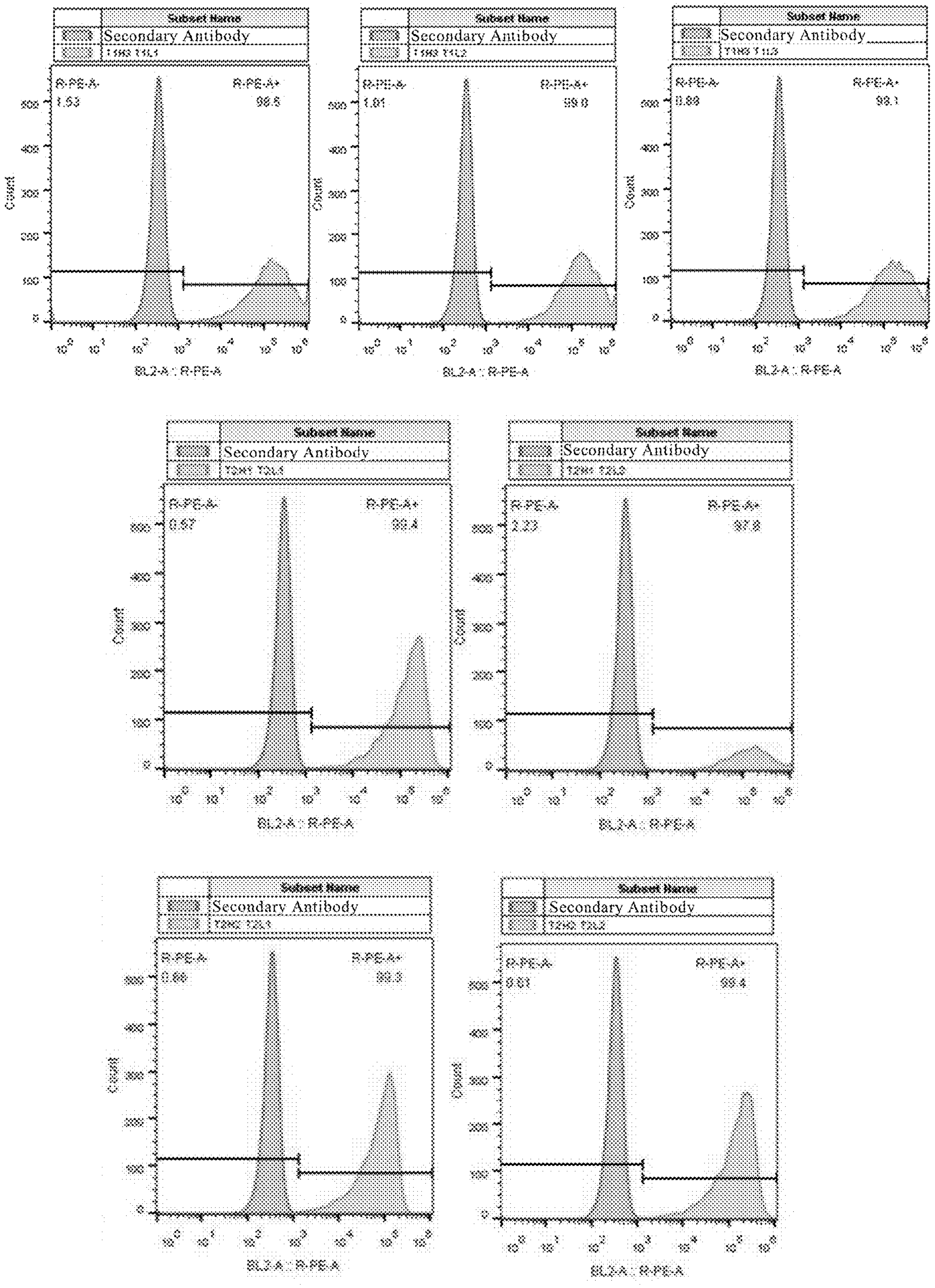

The FACS detection results are shown in FIG. 9. The humanized antibodies all bind to recombinant CHO-K 1-CD276 cells, and their binding ability is comparable to that of the human-mouse chimeric antibody. The expressed and purified antibodies of combination T1H1-T1L1 and T2H1-T2L1 were selected for subsequent affinity testing.

Figure 10:
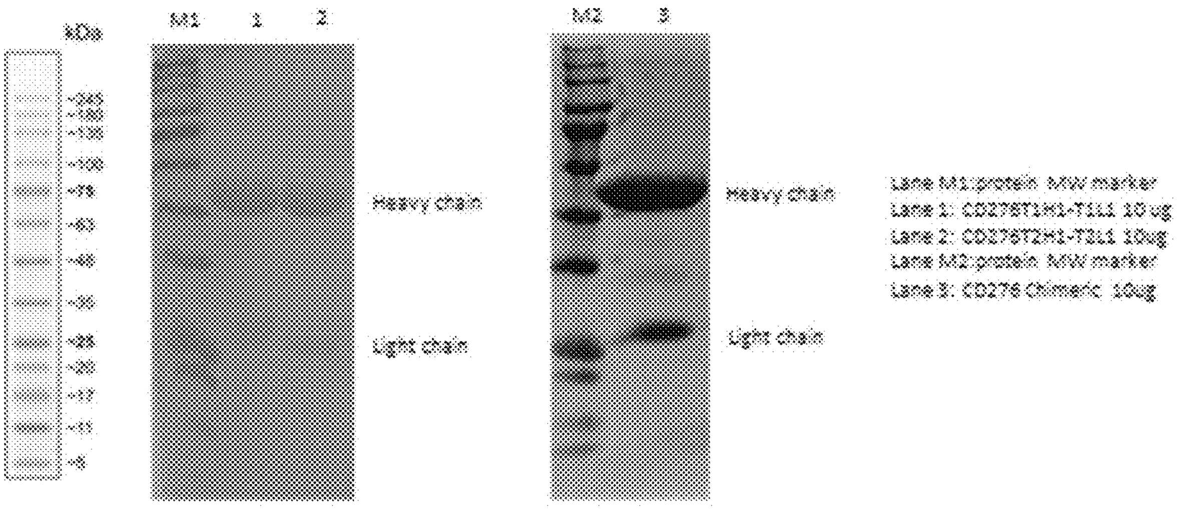
FIG. 10 shows the SDS-PAGE results of the humanized antibodies T1H1-T1L1 and T2H1-T2L1.

The SDS-PAGE results of the humanized antibodies T1H1-T1L1 and T2H1-T2L1 are shown in FIG. 10.

Figure 11:
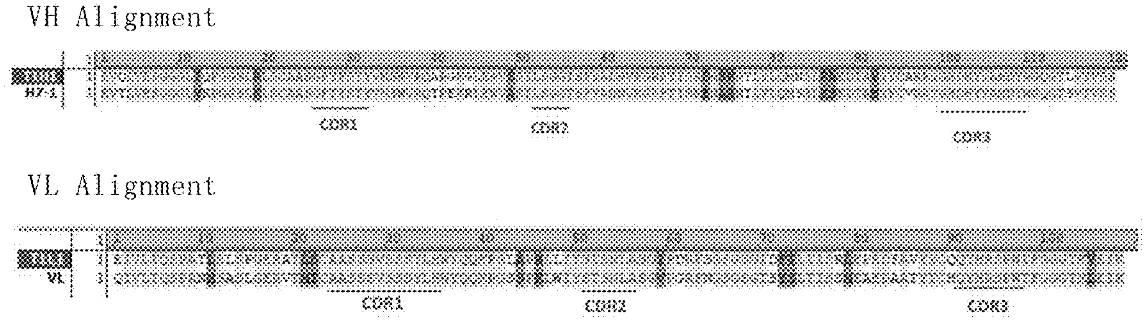
FIG. 11 shows the alignment result of humanized antibody T1H1-T1L1 and mouse derived antibody.
Figure 12:
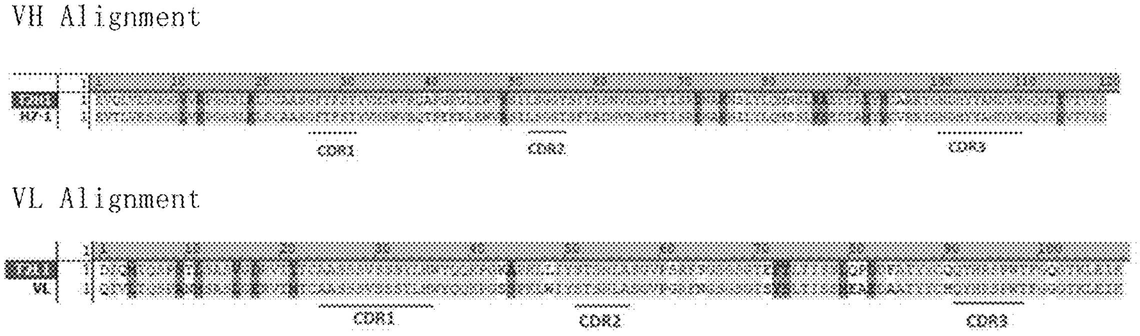
FIG. 12 shows the alignment result of humanized antibody T2H1-T2L1 and mouse derived antibody.

The sequences of non-humanized and humanized antibodies were compared. The alignment results of T1H1-T1L1 are shown in FIG. 11, and the alignment results of T2H1-T2L1 are shown in FIG. 12.

Example 8 Affinity Assay of Humanized Antibody 8.1 Experimental Materials and Reagents Involved in this Example S-series CM5 chip: GE, lot: 10261136

Buffer: HBS-EP+10×, GE, lot: BCBV7063, which was diluted 10 times with deionized water before use.

Amino coupling kit: GE, lot: 2067793

Regenerating reagent: 10 mM Glycine 1.5, GE, lot: 10240798

8.2 Ligand Coupling Preconcentration

Ligand: CD276 recombinant protein

Test pH: 10 mM Acetate 5.5/5.0/4.5/4.0

Flow rate: 10 μL/min

Buffer: HBS-EP+buffer

Figure 13:
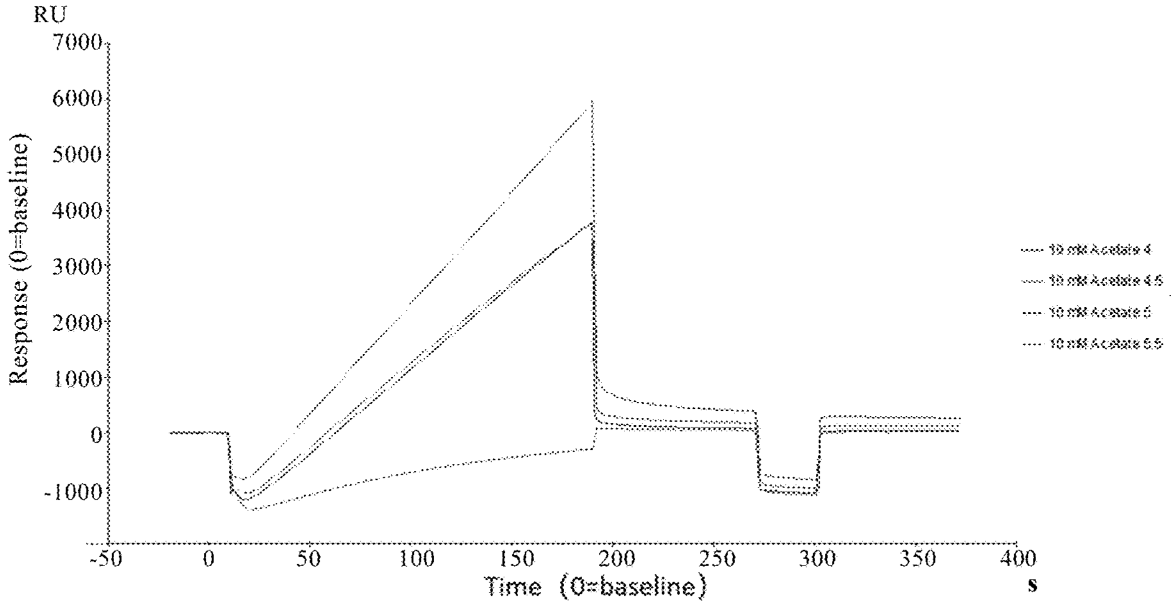
FIG. 13 shows the results of ligand coupling preconcentration.

The results are shown in FIG. 13. 10 mM of Acetate 4.0 was selected as the coupling buffer.

8.3 Ligand Coupling

Ligand: CD276 recombinant protein

Coupling buffer: 10 mM Acetate 4.0

Target coupling amount: 15 RU

Figure 14:
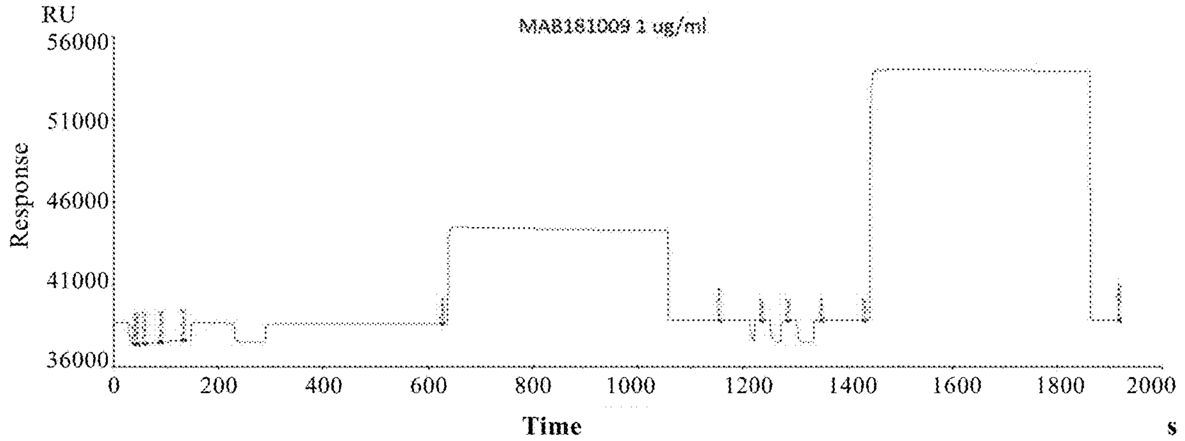
FIG. 14 shows the results of ligand coupling.

The result is shown in FIG. 14. The final coupling amount is 8.3 RU.

8.4 Affinity Assay of CD276 Chimeric, CD276T1H1-T1L1, CD276T2H1-T2L1 to CD276 Recombinant Protein Experimental conditions:

Antibody concentration: 1.5625/3.125/6.25/12.5/25/50 ug/ml

Flow rate: 30 μL/min

Binding time: 300 s

Dissociation time: 300 s

Regenerating reagent: Glycine 2.5

Figure 15:
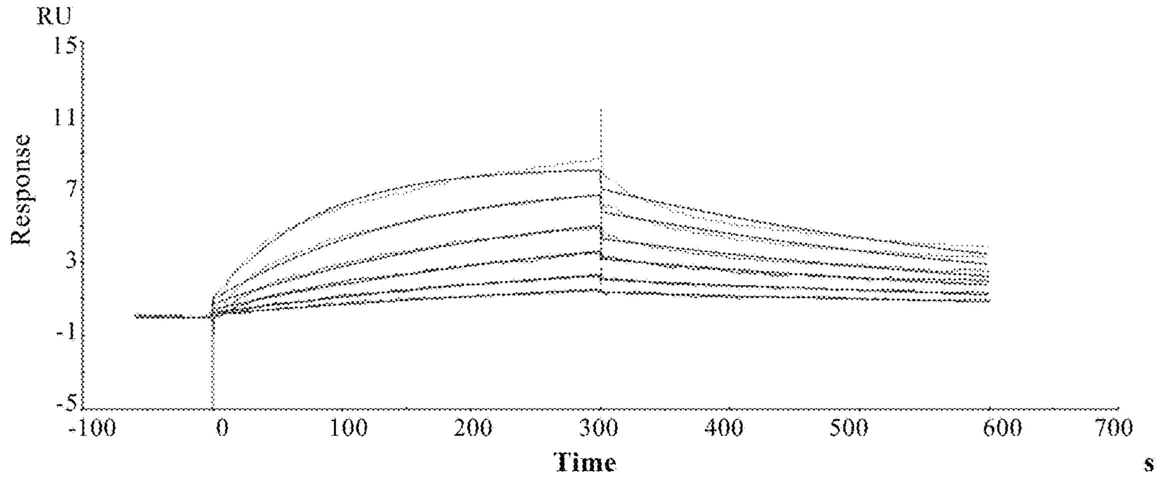
FIG. 15 shows the affinity determination results of CD276 Chimeric.
Figure 16:
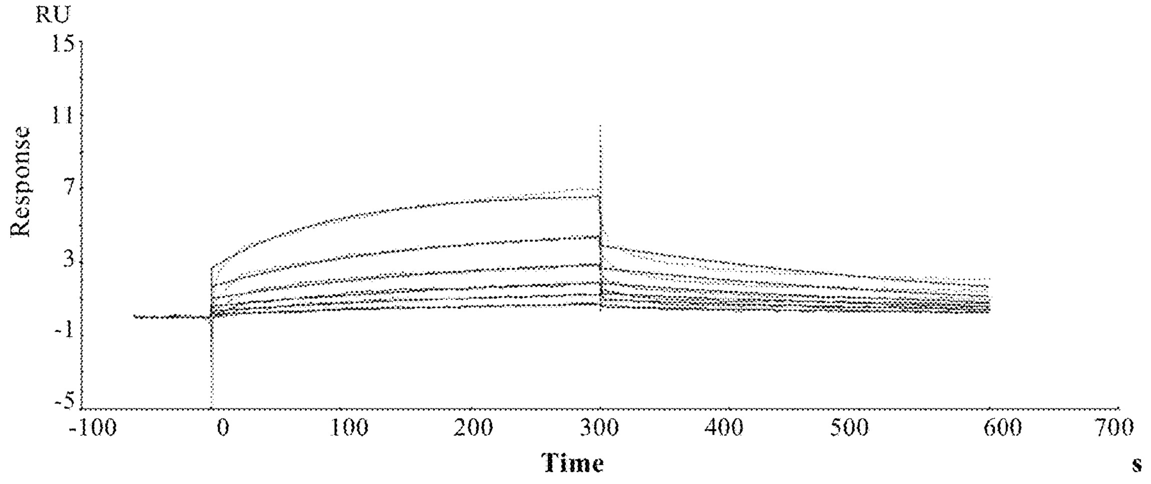
FIG. 16 shows the affinity determination results of CD276T1H1-T1L1.
Figure 17:
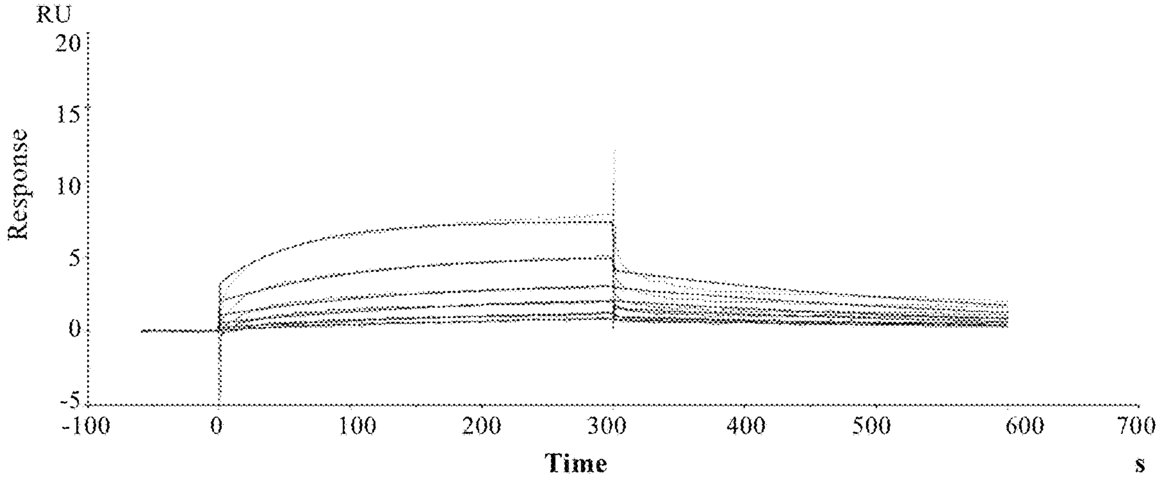
FIG. 17 shows the affinity determination results of CD276T2H1-T2L1.

The affinity assay results of CD276 Chimeric are shown in FIG. 15. The affinity assay results of CD276T1H1-T1L1 are shown in FIG. 16. The affinity assay results of CD276T2H1-T2L1 are shown in FIG. 17.

The affinity detection results of the antibodies are shown in Table 1.

TABLE 1

| | Ka ($M^{-1}$ $s^{-1}$) | Kd ($s^{-1}$) | KD (M) |
|---|---|---|---|
| CD276 Chimeric | $3.643 \times 10^4$ | 0.002581 | $7.083 \times 10^{-8}$ |
| CD276T1H1-T1L1 | $2.482 \times 10^4$ | 0.002823 | $1.138 \times 10^{-7}$ |
| CD276T2H1-T2L1 | $3.966 \times 10^4$ | 0.002887 | $7.279 \times 10^{-8}$ |

The affinity test results show that the affinity of humanized antibodies and chimeric antibodies were basically comparable.

Example 9 CD276 Antibody Membrane Proteome Array

The specificity and targeting of CD276 humanized antibody (CD276T1H1-T1L1) were tested using the Membrane Proteome Array method to determine if it has any off-target toxicity.

Membrane Proteome Array (MPA) is a platform that can analyze the specificity of antibodies or ligands targeting human membrane proteins, and MPA can be used to determine the targeting specificity of antibodies. This platform employs flow cytometry to directly detect the binding of antibodies to membrane proteins on unfixed cell surface. Therefore, all target proteins have the original natural conformation and appropriate post-translational modifications.

The humanized antibody CD276T1H1-T1L1 was detected using a library containing over 5300 human membrane proteins, including 94% of all single transmembrane proteins, multiple transmembrane proteins, and GPI-anchored proteins.

Figure 18:
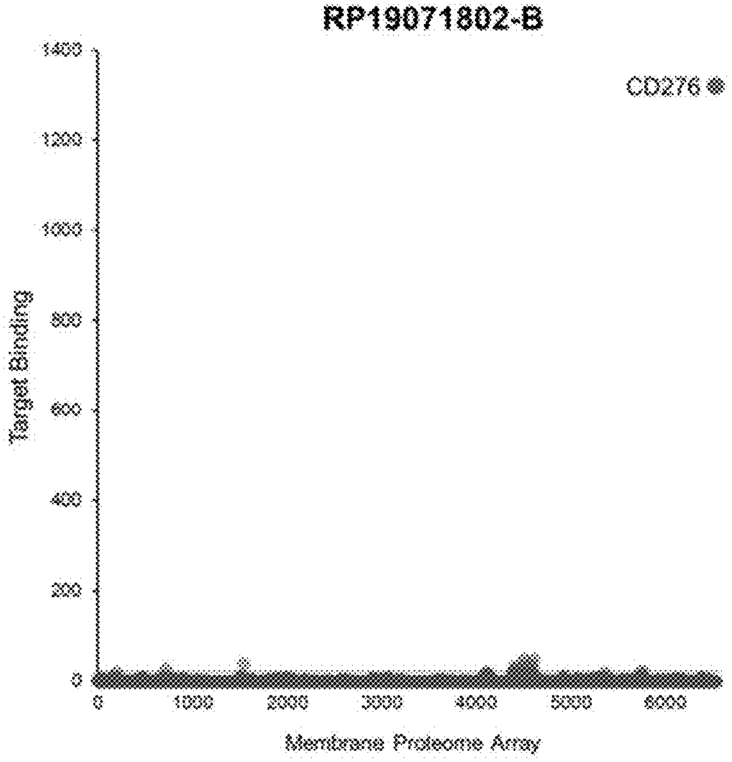
FIG. 18 shows the membrane proteome array detection results of humanized CD276 antibody (CD276T1H1-T1L1).

The results are shown in FIG. 18. The humanized CD276 antibody (CD276T1H1-T1L1) only binds specifically to CD276 protein and does not bind specifically to other membrane proteins, which indicates that the humanized CD276 antibody of the present invention only recognizes CD276 protein specifically, does not bind to other proteins, and does not cause off-target toxicity, further proving the specificity and safety of the humanized CD276 antibody of the present invention.

Example 10 Antigen Recognition Epitope of CD276 Humanized Antibody (CD276T1H1-T1L1)

10.1 Preparation of Vectors Expressing CD276 Antigen Fragments

The extracellular amino acid sequence information of the target antigen CD276 was analyzed, and truncated fragments of the antigen were designed. 10 amino acids was truncated in each fragment in sequence. Primers were designed to perform PCR, and the fragments were subcloned into the target vector Lenti-CMV-puro (using L2 signal peptide, MYRMQLLSCIALSLALVTNS (SEQ ID NO.: 31), and EcoRI digestion site).

The information of truncated amino acid sequences of CD276 are shown in Table 2.

TABLE 2

| CD276 truncated fragment | Amino acid sequence |
|---|---|
| Lenti-CD276(EPB1901)-puro 1-660 | SEQ ID NO: 32 |
| Lenti-CD276(EPB1901)-puro 30-660 | Positions 11-288 of SEQ ID NO: 32 |
| Lenti-CD276(EPB1901)-puro 60-660 | Positions 21-288 of SEQ ID NO: 32 |
| Lenti-CD276(EPB1901)-puro 90-660 | Positions 31-288 of SEQ ID NO: 32 |
| Lenti-CD276(EPB1901)-puro 120-660 | Positions 41-288 of SEQ ID NO: 32 |
| Lenti-CD276(EPB1901)-puro 150-660 | Positions 51-288 of SEQ ID NO: 32 |
| Lenti-CD276(EPB1901)-puro 180-660 | Positions 61-288 of SEQ ID NO: 32 |
| Lenti-CD276(EPB1901)-puro 210-660 | Positions 71-288 of SEQ ID NO: 32 |
| Lenti-CD276(EPB1901)-puro 240-660 | Positions 81-288 of SEQ ID NO: 32 |
| Lenti-CD276(EPB1901)-puro 270-660 | Positions 91-288 of SEQ ID NO: 32 |
| Lenti-CD276(EPB1901)-puro 300-660 | Positions 101-288 of SEQ ID NO: 32 |
| Lenti-CD276(EPB1901)-puro 330-660 | Positions 111-288 of SEQ ID NO: 32 |
| Lenti-CD276(EPB1901)-puro 360-660 | Positions 121-288 of SEQ ID NO: 32 |
| Lenti-CD276(EPB1901)-puro 390-660 | Positions 131-288 of SEQ ID NO: 32 |
| Lenti-CD276(EPB1901)-puro 420-660 | Positions 141-288 of SEQ ID NO: 32 |
| Lenti-CD276(EPB1901)-puro 450-660 | Positions 151-288 of SEQ ID NO: 32 |
| Lenti-CD276(EPB1901)-puro 480-660 | Positions 161-288 of SEQ ID NO: 32 |
| Lenti-CD276(EPB1901)-puro 510-660 | Positions 171-288 of SEQ ID NO: 32 |
| Lenti-CD276(EPB1901)-puro 540-660 | Positions 181-288 of SEQ ID NO: 32 |
| Lenti-CD276(EPB1901)-puro 570-660 | Positions 191-288 of SEQ ID NO: 32 |
| Lenti-CD276(EPB1901)-puro 600-660 | Positions 201-288 of SEQ ID NO: 32 |
| Lenti-CD276(EPB1901)-puro 630-660 | Positions 211-288 of SEQ ID NO: 32 |

10.2 Expression and Flow Cytometry-Detection of Different Truncated CD276

1. LVTransm transfection reagent and antibody expression vectors were taken from the refrigerator, thawed at room temperature, and then blown up and down with a pipette until well mixed. PBS buffer was taken out and warmed to room temperature. 0.5 mL of PBS was taken into one hole of the 6-well plate and added with 6 μg expression vectors of different truncated CD276 respectively, blown up and down with a pipette until well mixed, then added with 18 μL of LVTransm and immediately blown up and down with a pipette until well mixed, then it was placed at room temperature for 10 minutes.
2. The above DNA/LVTransm complex was added into 1.5 mL of 293F cells, gently shaken until well mixed. The cells were placed in a 37° C., 5% CO2 incubator and cultured at 130 RPM for 6-8 hours. Then 1.5 mL of fresh FreeStyle™ 293 Expression Medium was added, and the cells were returned to the incubator for further cultivation.
3. After continuous cultivation for 48 hours, cells were centrifuged and collected separately for flow cytometry detection.

10.3 Flow Cytometry-Detection of CD276 Antibodies Binding to Different Truncated Antigens 1. Cells transfected in step 10.2 were collected and each type of cell was divided into 2 sections with $5\times10^5$ cells in each section.
2. CD276 antibodies were incubated separately (1 ug/well), mixed well, and incubated at room temperature for 1 hour.
3. The cells were centrifuged at 800×g at room temperature for 5 minutes, the supernatant containing antibodies was discarded, and the cells were washed 3 times with PBS.
4. 1 μl of PE-labeled Anti-Human IgG was added, mixed well, and incubated at room temperature in dark for 30 min.
5. The cells were centrifuged at 800×g at room temperature for 5 minutes, the supernatant containing the secondary antibodies was discarded, and the cells were washed 3 times with PBS.
6. The cells were resuspended in 500 μL of PBS, and then subjected to the flow cytometry.

Figure 19:
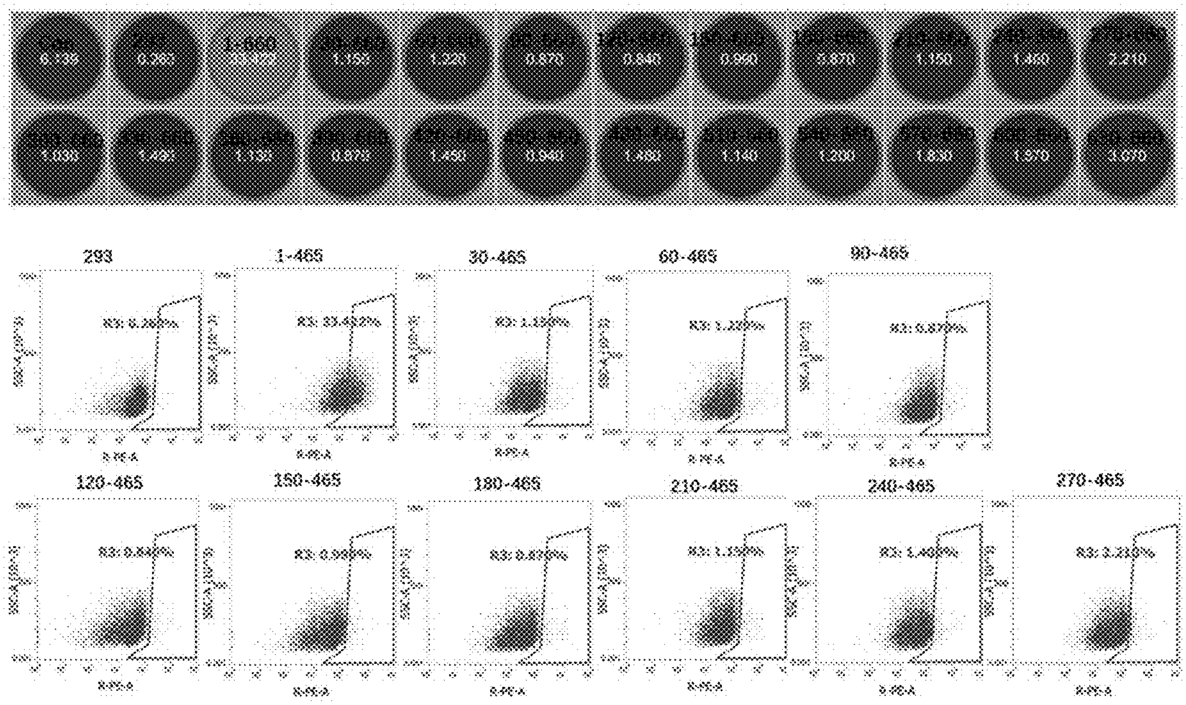
FIG. 19 shows the flow cytometry results of CD276 antibodies binding to different truncated antigens.
Figure 19:
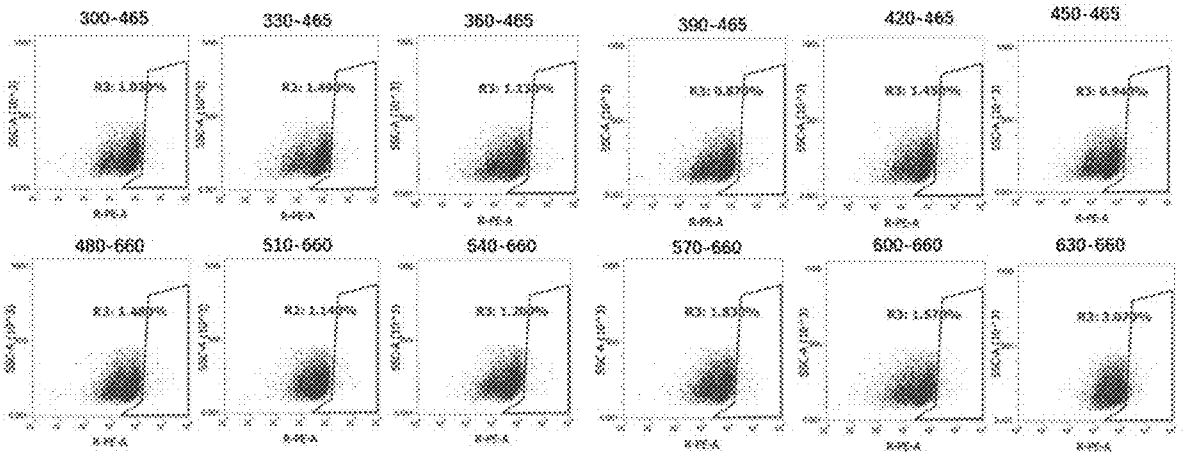

The flow cytometry results are shown in FIG. 19. The antigen epitope of CD276 is located in the first 10 amino acids of the extracellular fragment. Through prediction analysis of signal peptide, two more amino acids will be cleaved at the cleavage position of IL2 signal peptide, so the antigen epitope should be between 3-12 amino acids.

In order to ensure the structural integrity of the antigen, further antigen epitope detection will be carried out through a point mutation scheme; each amino acid will be mutated into a Gly with the smallest side chain. Subsequent experimental design involved point mutations of 3-12 amino acids in the antigen, with each site mutated into a Gly. After gene synthesis, they were subcloned to *Lenti*-CMV-puro to construct antigen mutation vectors.

Figure 20:
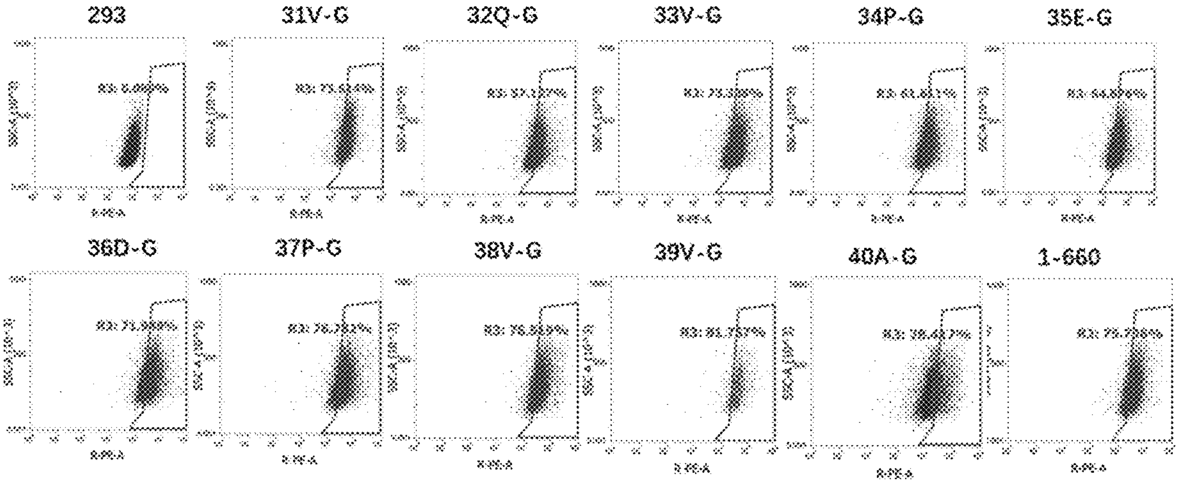
FIG. 20 shows the flow cytometry results of CD276 antibody binding to antigens with different site mutations.

The flow cytometry results of CD276 antibody binding to antigens with different site mutations are shown in FIG. 20. The results showed that the antigen epitopes of CD276 antibody were mainly in the $31^{th}$-$40^{th}$ amino acids, with the main sites being 32Q and 40A.

The antigen epitopes are shown as follows (where the italic sequence is the signal peptide, and the bold and underlined sequence is the antigen recognition epitope of CD276 antibody):

(SEQ ID NO.: 33)

*MLRRRGSPGMGVHVGAALGALWFCLTGA*LEVQVPEDPVVALVGTDATLC

CSFSPEPGFSLAQLNLIWQLTDTKQLVHSFAEGQDQGSAYANRTALFPD

LLAQGNASLRLQRVRVADEGSFTCFVSIRDFGSAAVSLQVAAPYSKPSM

TLEPNKDLRPGDTVTITCSSYRGYPEAEVFWQDGQGVPLTGNVTTSQMA

NEQGLFDVHSVLRVVLGANGTYSCLVRNPVLQQDAHGSVTITGQPMTFP

PEALWVTVGLSVCLIALLVALAFVCWRKIKQSCEEENAGAEDQDGEGEG

SKTALQPLKHSDSKEDDGQEIA

All documents mentioned in the present invention are incorporated by reference herein as if each document were incorporated separately by reference. Furthermore, it should be understood that after reading the foregoing teachings of the invention, various changes or modifications may be made to the invention by those skilled in the art and that these equivalents are equally within the scope of the claims appended to this application.

The invention claimed is:

1. An antibody targeting CD276 comprising:

(1) a heavy chain variable region of an antibody, which comprises following three complementarity determining regions (CDRs):

a CDR1 set forth in SEQ ID NO: 1, a CDR2 set forth in SEQ ID NO: 2, and a CDR3 set forth in SEQ ID NO: 3 or 7; and (2) a light chain variable region of an antibody, which comprises following three complementarity determining regions (CDRs):

a CDR1' set forth in SEQ ID NO: 4, a CDR2' set forth in SEQ ID NO: 5, and a CDR3' set forth in SEQ ID NO: 6;.

2. The antibody according to claim 1, wherein the antibody is selected from the group consisting of a chimeric antibody and a humanized antibody.

3. The antibody according to claim 1, wherein the sequence of the heavy chain variable region of the antibody is shown in SEQ ID NO: 8, 9, or 26-30; and/or the sequence of the light chain variable region of the antibody is shown in SEQ ID NO: 10, or 21-25.

4. A CAR construct, wherein the CAR construct comprises an scFv specifically binding to CD276, and the scFv comprises a heavy chain variable region of an antibody, which comprises following three complementarity determining regions (CDRs):

a CDR1 set forth in SEQ ID NO: 1, a CDR2 set forth in SEQ ID NO: 2, and a CDR3 set forth in SEQ ID NO: 3 or 7 and a light chain variable region of an antibody, which comprises following three complementarity determining regions (CDRs):

a CDR1' set forth in SEQ ID NO: 4, a CDR2' set forth in SEQ ID NO: 5, and a CDR3' set forth in SEQ ID NO: 6.

5. A recombinant immune cell expressing an exogenous CAR construct according to claim 4.

6. The antibody according to claim 1, wherein the sequence of the heavy chain variable region of the antibody is shown in SEQ ID NO: 8 or 9; and the sequence of the light chain variable region of the antibody is shown in SEQ ID NO: 10.

7. The antibody according to claim 1, wherein the sequence of the heavy chain variable region of the antibody is shown in SEQ ID NO: 26; and the sequence of the light chain variable region of the antibody is shown in SEQ ID NO: 21.

8. The antibody according to claim 1, wherein sequence of the heavy chain variable region of the antibody is shown in SEQ ID NO: 29; and the sequence of the light chain variable region of the antibody is shown in SEQ ID NO: 24.

9. A method for treating a CD276-positive tumor, wherein the method comprises administering an antibody targeting CD276, an antibody-drug conjugate of the antibody, or a CAR-T cell expressing the antibody, to a subject in need thereof, wherein the antibody targeting CD276 comprises:

(1) a heavy chain variable region of an antibody, which comprises following three complementarity determining regions (CDRs):

a CDR1 set forth in SEQ ID NO: 1, a CDR2 set forth in SEQ ID NO: 2, and a CDR3 set forth in SEQ ID NO: 3 or 7; and (2) a light chain variable region of an antibody, which comprises following three complementarity determining regions (CDRs):

a CDR1' set forth in SEQ ID NO: 4, a CDR2' set forth in SEQ ID NO: 5, and a CDR3' set forth in SEQ ID NO: 6.

* * * * *

SEQUENCE LISTING

<160> NUMBER OF SEQ ID NOS: 33

<210> SEQ ID NO 1
<211> LENGTH: 7
<212> TYPE: PRT
<213> ORGANISM: Mus musculus

<400> SEQUENCE: 1

Gly Phe Thr Phe Ser Thr Tyr
1 5

<210> SEQ ID NO 2
<211> LENGTH: 5
<212> TYPE: PRT
<213> ORGANISM: Mus musculus

<400> SEQUENCE: 2

Leu Ser Gly Gly Thr
1 5

<210> SEQ ID NO 3
<211> LENGTH: 12
<212> TYPE: PRT
<213> ORGANISM: Mus musculus

<400> SEQUENCE: 3

Arg Tyr Gly His Asp His Tyr Tyr Ala Met Asp Tyr
1 5 10

<210> SEQ ID NO 4
<211> LENGTH: 12
<212> TYPE: PRT
<213> ORGANISM: Mus musculus

<400> SEQUENCE: 4

Ala Ala Ser Ser Ser Val Ser Ser Ser Tyr Leu His
1 5 10

<210> SEQ ID NO 5
<211> LENGTH: 7
<212> TYPE: PRT
<213> ORGANISM: Mus musculus

<400> SEQUENCE: 5

Ser Thr Ser Asn Leu Ala Ser
1 5

<210> SEQ ID NO 6
<211> LENGTH: 8
<212> TYPE: PRT
<213> ORGANISM: Mus musculus

<400> SEQUENCE: 6

Gln Tyr His Arg Ser Pro Trp Thr
1 5

<210> SEQ ID NO 7
<211> LENGTH: 12
<212> TYPE: PRT
<213> ORGANISM: Mus musculus

<400> SEQUENCE: 7

Arg Tyr Gly His Asp Arg Tyr Tyr Ala Met Asp Tyr
1 5 10

<210> SEQ ID NO 8
<211> LENGTH: 120
<212> TYPE: PRT
<213> ORGANISM: Mus musculus

<400> SEQUENCE: 8

```
Glu Val Thr Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Thr Tyr
            20                  25                  30

Val Met Ser Trp Val Arg Gln Thr Pro Glu Lys Arg Leu Glu Trp Val
        35                  40                  45

Ala Ser Ile Leu Ser Gly Gly Thr Ser Phe Tyr Ala Asp Asn Val Lys
    50                  55                  60

Gly Arg Phe Thr Ile Ser Arg Glu Asn Ala Arg Asn Ile Leu Tyr Leu
65                  70                  75                  80

Gln Met Ser Ser Leu Lys Ser Glu Asp Thr Ala Met Tyr Tyr Cys Val
                85                  90                  95

Arg Arg Tyr Gly His Asp Arg Tyr Tyr Ala Met Asp Tyr Trp Gly Gln
            100                 105                 110

Gly Thr Ser Val Thr Val Ser Ser
        115                 120
```

<210> SEQ ID NO 9
<211> LENGTH: 120
<212> TYPE: PRT
<213> ORGANISM: Mus musculus

<400> SEQUENCE: 9

```
Glu Val Thr Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Thr Tyr
            20                  25                  30

Val Met Ser Trp Val Arg Gln Thr Pro Glu Lys Arg Leu Glu Trp Val
        35                  40                  45

Ala Ser Ile Leu Ser Gly Gly Thr Ser Phe Tyr Ala Asp Asn Val Lys
    50                  55                  60

Gly Arg Phe Thr Ile Ser Arg Glu Asn Ala Arg Asn Ile Leu Tyr Leu
65                  70                  75                  80

Gln Met Ser Ser Leu Lys Ser Glu Asp Thr Ala Met Tyr Tyr Cys Val
                85                  90                  95

Arg Arg Tyr Gly His Asp His Tyr Tyr Ala Met Asp Tyr Trp Gly Gln
            100                 105                 110

Gly Thr Ser Val Thr Val Ser Ser
        115                 120
```

<210> SEQ ID NO 10
<211> LENGTH: 108
<212> TYPE: PRT
<213> ORGANISM: Mus musculus

<400> SEQUENCE: 10

```
Gln Ile Val Leu Thr Gln Ser Pro Ala Asn Met Ser Ala Ser Leu Gly
1               5                   10                  15

Glu Arg Val Thr Met Thr Cys Ala Ala Ser Ser Ser Val Ser Ser Ser
            20                  25                  30

Tyr Leu His Trp Tyr Gln Gln Lys Pro Gly Ser Ser Pro Lys Leu Trp
```

```
        35                  40                  45

Ile Tyr Ser Thr Ser Asn Leu Ala Ser Gly Val Pro Gly Arg Phe Asn
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln Tyr His Arg Ser Pro
                85                  90                  95

Trp Thr Phe Gly Gly Gly Thr Lys Leu Glu Ile Lys
            100                 105


<210> SEQ ID NO 11
<211> LENGTH: 324
<212> TYPE: DNA
<213> ORGANISM: Artificial Sequence
<220> FEATURE:
<223> OTHER INFORMATION: Humanized antibody (T1L1)

<400> SEQUENCE: 11

gagatcgtgc tgacacagtc tcccgccaca ctgtcactgt ctccaggcga aagagccaca     60

ctgagctgcg ctgcctctag ctctgtgtcc agcagctacc tgcactggta tcagcagaag    120

cctggactgg cccctcggct gctgatctac agcacaagca atctggccag cggcatcccc    180

gatagatttt ccggctctgg ctccggcacc gacttcaccc tgacaatcag cagactggaa    240

cccgaggact tcgccgtgta ctactgccag cagtaccaca gaagcccctg gacatttggc    300

ggaggcacca aggtggaaat caag                                           324


<210> SEQ ID NO 12
<211> LENGTH: 324
<212> TYPE: DNA
<213> ORGANISM: Artificial Sequence
<220> FEATURE:
<223> OTHER INFORMATION: Humanized antibody (T1L2)

<400> SEQUENCE: 12

gagatcgtgc tgacacagtc tcccgccaca ctgtcactgt ctccaggcga aagagccaca     60

ctgagctgcg ctgcctctag ctctgtgtcc agcagctacc tgcactggta tcagcagaag    120

cctggcagcg ctcccagact gctgatctac agcacaagca atctggccag cggcatcccc    180

gatagatttt ccggctctgg ctccggcacc gacttcaccc tgacaatcag cagactggaa    240

cccgaggact tcgccgtgta ctactgccag cagtaccaca gaagcccctg gacatttggc    300

ggaggcacca aggtggaaat caag                                           324


<210> SEQ ID NO 13
<211> LENGTH: 324
<212> TYPE: DNA
<213> ORGANISM: Artificial Sequence
<220> FEATURE:
<223> OTHER INFORMATION: Humanized antibody (T1L3)

<400> SEQUENCE: 13

gagatcgtgc tgacacagtc tcccgccaca ctgtcactgt ctccaggcga aagagccaca     60

ctgagctgcg ctgcctctag ctctgtgtcc agcagctacc tgcactggta tcagcagaag    120

cctggcagcg ctcccagact gctgatctac agcacaagca atctggccag cggcatcccc    180

gatagatttt ccggctctgg ctccggcacc gacttcaccc tgacaatctc tagactggaa    240

gccgaggact tcgccgtgta ctactgccag cagtaccaca gaagcccctg gacatttggc    300

ggaggcacca aggtggaaat caag                                           324
```

<210> SEQ ID NO 14
<211> LENGTH: 324
<212> TYPE: DNA
<213> ORGANISM: Artificial Sequence
<220> FEATURE:
<223> OTHER INFORMATION: Humanized antibody (T2L1)

<400> SEQUENCE: 14
gacatccaga tgacacagag ccccagcaca ctgtctgcca gcgtgggaga cagagtgacc 60
attacatgtg ccgccagcag cagcgtgtcc agctcttacc tgcactggta tcagcagaag 120
cccggcaagg cccctaagct gctgatctac agcaccagca atctggccag cggcgtgcca 180
agcagatttt ctggctctgg cagcggcacc gagttcaccc tgaccatctc tagcctgcag 240
cctgacgact tcgccaccta ctactgccag cagtaccaca gaagcccctg gacatttggc 300
cagggcacca agctggaaat caag 324

<210> SEQ ID NO 15
<211> LENGTH: 324
<212> TYPE: DNA
<213> ORGANISM: Artificial Sequence
<220> FEATURE:
<223> OTHER INFORMATION: Humanized antibody (T2L2)

<400> SEQUENCE: 15
gacatccaga tgacacagag ccccagcaca ctgtctgcca gcgtgggaga cagagtgacc 60
attacatgtg ccgccagcag cagcgtgtcc agctcttacc tgcactggta tcagcagaag 120
cccggcaagg cccctaagct gctgatctac agcaccagca atctggccag cggcgtgcca 180
agcagatttt ctggctctgg cagcggcacc gagttcaccc tgaccatctc tagcctgcag 240
cctgatgatg ccgccaccta ctactgccag cagtaccaca gaagcccctg gacatttggc 300
cagggcacca agctggaaat caag 324

<210> SEQ ID NO 16
<211> LENGTH: 360
<212> TYPE: DNA
<213> ORGANISM: Artificial Sequence
<220> FEATURE:
<223> OTHER INFORMATION: Humanized antibody (T1H1)

<400> SEQUENCE: 16
gaggtgcagc tggttgaatc tggcggcgga ctgattcagc ctggcggatc tctgagactg 60
agctgtgccg ccagcggctt cacctttagc acctacgtga tgagctgggt ccgacaggcc 120
cctggcaaag gacttgaatg ggtgtccagc atcctgagcg gcggcacaag cttctacgcc 180
gacaatgtga agggcagatt caccatcagc cgggacaaca gcaagaacac cctgtacctg 240
cagatgaaca gcctgagagc cgaggacacc gccgtgtact actgcgccag aagatacggc 300
cacgaccact actacgccat ggactattgg ggccagggca ccctggttac cgttagctct 360

<210> SEQ ID NO 17
<211> LENGTH: 360
<212> TYPE: DNA
<213> ORGANISM: Artificial Sequence
<220> FEATURE:
<223> OTHER INFORMATION: Humanized antibody (T1H2)

<400> SEQUENCE: 17
gaggtgcagc tggttgaatc tggcggcgga ctgattcagc ctggcggatc tctgagactg 60
agctgtgccg ccagcggctt cacctttagc acctacgtga tgagctgggt ccgacagaca 120
cctggcaaag gcctggaatg ggtgtccagc attctgagcg gcggcaccag cttctacgcc 180
gacaatgtga agggcagatt caccatcagc cgggacaaca gcaagaacac cctgtacctg 240
cagatgaaca gcctgagagc cgaggacacc gccgtgtact actgcgccag aagatacggc 300
cacgaccact actacgccat ggactattgg ggccagggca ccctggttac cgttagctct 360

<210> SEQ ID NO 18
<211> LENGTH: 360
<212> TYPE: DNA
<213> ORGANISM: Artificial Sequence
<220> FEATURE:
<223> OTHER INFORMATION: Humanized antibody (T1H3)

<400> SEQUENCE: 18
gaggtgcagc tggttgaatc tggcggcgga ctgattcagc ctggcggatc tctgagactg 60
agctgtgccg ccagcggctt cacctttagc acctacgtga tgagctgggt ccgacagaca 120
cctggcaaag gcctggaatg ggtgtccagc attctgagcg gcggcaccag cttctacgcc 180
gacaatgtga agggcagatt caccatcagc cgggacaaca gcaagaacac cctgtacctg 240
cagatgaaca gcctgagagc cgaggacacc gccatgtact actgcgccag aagatacggc 300
cacgaccact actacgccat ggattattgg ggccagggca ccctggtcac cgtttcttct 360

<210> SEQ ID NO 19
<211> LENGTH: 360
<212> TYPE: DNA
<213> ORGANISM: Artificial Sequence
<220> FEATURE:
<223> OTHER INFORMATION: Humanized antibody (T2H1)

<400> SEQUENCE: 19
gaggtgcagc tggttgaatc tggtggcggc gttgtcagac ctggcggatc tctgagactg 60
agctgtgccg ccagcggctt cacctttagc acctacgtga tgagctgggt ccgacaggcc 120
cctggcaaag gacttgaatg ggtgtccagc atcctgagcg gcggcacaag cttctacgcc 180
gacaatgtga agggcagatt caccatcagc cgggacaacg ccaagaacag cctgtacctg 240
cagatgaact ccctgagagc cgaggacaca gccctgtatc actgcgccag aagatacggc 300
cacgaccact actacgccat ggactattgg ggccagggca ccaccgtgac agtctcttct 360

<210> SEQ ID NO 20
<211> LENGTH: 360
<212> TYPE: DNA
<213> ORGANISM: Artificial Sequence
<220> FEATURE:
<223> OTHER INFORMATION: Humanized antibody (T2H2)

<400> SEQUENCE: 20
gaggtgcagc tggttgaatc tggtggcggc gttgtcagac ctggcggatc tctgagactg 60
agctgtgccg ccagcggctt cacctttagc acctacgtga tgagctgggt ccgacagaca 120
cctggcaaag gcctggaatg ggtgtccagc attctgagcg gcggcaccag cttctacgcc 180
gacaatgtga agggcagatt caccatcagc cgggacaacg ccaagaacag cctgtacctg 240
cagatgaact ccctgagagc cgaggacaca gccctgtatc actgcgccag aagatacggc 300
cacgaccact actacgccat ggactattgg ggccagggca ccaccgtgac agtctcttct 360

<210> SEQ ID NO 21
<211> LENGTH: 108

<212> TYPE: PRT
<213> ORGANISM: Artificial Sequence
<220> FEATURE:
<223> OTHER INFORMATION: Humanized antibody (T1L1)

<400> SEQUENCE: 21

```
Glu Ile Val Leu Thr Gln Ser Pro Ala Thr Leu Ser Leu Ser Pro Gly
1               5                   10                  15

Glu Arg Ala Thr Leu Ser Cys Ala Ala Ser Ser Ser Val Ser Ser Ser
            20                  25                  30

Tyr Leu His Trp Tyr Gln Gln Lys Pro Gly Leu Ala Pro Arg Leu Leu
        35                  40                  45

Ile Tyr Ser Thr Ser Asn Leu Ala Ser Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr His Arg Ser Pro
                85                  90                  95

Trp Thr Phe Gly Gly Gly Thr Lys Val Glu Ile Lys
            100                 105
```

<210> SEQ ID NO 22
<211> LENGTH: 108
<212> TYPE: PRT
<213> ORGANISM: Artificial Sequence
<220> FEATURE:
<223> OTHER INFORMATION: Humanized antibody (T1L2)

<400> SEQUENCE: 22

```
Glu Ile Val Leu Thr Gln Ser Pro Ala Thr Leu Ser Leu Ser Pro Gly
1               5                   10                  15

Glu Arg Ala Thr Leu Ser Cys Ala Ala Ser Ser Ser Val Ser Ser Ser
            20                  25                  30

Tyr Leu His Trp Tyr Gln Gln Lys Pro Gly Ser Ala Pro Arg Leu Leu
        35                  40                  45

Ile Tyr Ser Thr Ser Asn Leu Ala Ser Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr His Arg Ser Pro
                85                  90                  95

Trp Thr Phe Gly Gly Gly Thr Lys Val Glu Ile Lys
            100                 105
```

<210> SEQ ID NO 23
<211> LENGTH: 108
<212> TYPE: PRT
<213> ORGANISM: Artificial Sequence
<220> FEATURE:
<223> OTHER INFORMATION: Humanized antibody (T1L3)

<400> SEQUENCE: 23

```
Glu Ile Val Leu Thr Gln Ser Pro Ala Thr Leu Ser Leu Ser Pro Gly
1               5                   10                  15

Glu Arg Ala Thr Leu Ser Cys Ala Ala Ser Ser Ser Val Ser Ser Ser
            20                  25                  30

Tyr Leu His Trp Tyr Gln Gln Lys Pro Gly Ser Ala Pro Arg Leu Leu
        35                  40                  45

Ile Tyr Ser Thr Ser Asn Leu Ala Ser Gly Ile Pro Asp Arg Phe Ser
```

```
    50                  55                  60

Gly Ser Gly Ser Gly Thr Asp Phe Thr Leu Thr Ile Ser Arg Leu Glu
65                  70                  75                  80

Ala Glu Asp Phe Ala Val Tyr Tyr Cys Gln Gln Tyr His Arg Ser Pro
                85                  90                  95

Trp Thr Phe Gly Gly Gly Thr Lys Val Glu Ile Lys
            100                 105


<210> SEQ ID NO 24
<211> LENGTH: 108
<212> TYPE: PRT
<213> ORGANISM: Artificial Sequence
<220> FEATURE:
<223> OTHER INFORMATION: Humanized antibody (T2L1)

<400> SEQUENCE: 24

Asp Ile Gln Met Thr Gln Ser Pro Ser Thr Leu Ser Ala Ser Val Gly
1               5                   10                  15

Asp Arg Val Thr Ile Thr Cys Ala Ala Ser Ser Ser Val Ser Ser Ser
            20                  25                  30

Tyr Leu His Trp Tyr Gln Gln Lys Pro Gly Lys Ala Pro Lys Leu Leu
        35                  40                  45

Ile Tyr Ser Thr Ser Asn Leu Ala Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Asp Asp Phe Ala Thr Tyr Tyr Cys Gln Gln Tyr His Arg Ser Pro
                85                  90                  95

Trp Thr Phe Gly Gln Gly Thr Lys Leu Glu Ile Lys
            100                 105


<210> SEQ ID NO 25
<211> LENGTH: 108
<212> TYPE: PRT
<213> ORGANISM: Artificial Sequence
<220> FEATURE:
<223> OTHER INFORMATION: Humanized antibody (T2L2)

<400> SEQUENCE: 25

Asp Ile Gln Met Thr Gln Ser Pro Ser Thr Leu Ser Ala Ser Val Gly
1               5                   10                  15

Asp Arg Val Thr Ile Thr Cys Ala Ala Ser Ser Ser Val Ser Ser Ser
            20                  25                  30

Tyr Leu His Trp Tyr Gln Gln Lys Pro Gly Lys Ala Pro Lys Leu Leu
        35                  40                  45

Ile Tyr Ser Thr Ser Asn Leu Ala Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Asp Asp Ala Ala Thr Tyr Tyr Cys Gln Gln Tyr His Arg Ser Pro
                85                  90                  95

Trp Thr Phe Gly Gln Gly Thr Lys Leu Glu Ile Lys
            100                 105


<210> SEQ ID NO 26
<211> LENGTH: 120
<212> TYPE: PRT
<213> ORGANISM: Artificial Sequence
<220> FEATURE:
```

<223> OTHER INFORMATION: Humanized antibody (T1H1)

<400> SEQUENCE: 26

Glu Val Gln Leu Val Glu Ser Gly Gly Gly Leu Ile Gln Pro Gly Gly
1 5 10 15

Ser Leu Arg Leu Ser Cys Ala Ala Ser Gly Phe Thr Phe Ser Thr Tyr
20 25 30

Val Met Ser Trp Val Arg Gln Ala Pro Gly Lys Gly Leu Glu Trp Val
35 40 45

Ser Ser Ile Leu Ser Gly Gly Thr Ser Phe Tyr Ala Asp Asn Val Lys
50 55 60

Gly Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Ala
85 90 95

Arg Arg Tyr Gly His Asp His Tyr Tyr Ala Met Asp Tyr Trp Gly Gln
100 105 110

Gly Thr Leu Val Thr Val Ser Ser
115 120

<210> SEQ ID NO 27
<211> LENGTH: 120
<212> TYPE: PRT
<213> ORGANISM: Artificial Sequence
<220> FEATURE:
<223> OTHER INFORMATION: Humanized antibody (T1H2)

<400> SEQUENCE: 27

Glu Val Gln Leu Val Glu Ser Gly Gly Gly Leu Ile Gln Pro Gly Gly
1 5 10 15

Ser Leu Arg Leu Ser Cys Ala Ala Ser Gly Phe Thr Phe Ser Thr Tyr
20 25 30

Val Met Ser Trp Val Arg Gln Thr Pro Gly Lys Gly Leu Glu Trp Val
35 40 45

Ser Ser Ile Leu Ser Gly Gly Thr Ser Phe Tyr Ala Asp Asn Val Lys
50 55 60

Gly Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Ala
85 90 95

Arg Arg Tyr Gly His Asp His Tyr Tyr Ala Met Asp Tyr Trp Gly Gln
100 105 110

Gly Thr Leu Val Thr Val Ser Ser
115 120

<210> SEQ ID NO 28
<211> LENGTH: 120
<212> TYPE: PRT
<213> ORGANISM: Artificial Sequence
<220> FEATURE:
<223> OTHER INFORMATION: Humanized antibody (T1H3)

<400> SEQUENCE: 28

Glu Val Gln Leu Val Glu Ser Gly Gly Gly Leu Ile Gln Pro Gly Gly
1 5 10 15

Ser Leu Arg Leu Ser Cys Ala Ala Ser Gly Phe Thr Phe Ser Thr Tyr
20 25 30

Val Met Ser Trp Val Arg Gln Thr Pro Gly Lys Gly Leu Glu Trp Val

```
        35                  40                  45

Ser Ser Ile Leu Ser Gly Gly Thr Ser Phe Tyr Ala Asp Asn Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Met Tyr Tyr Cys Ala
                85                  90                  95

Arg Arg Tyr Gly His Asp His Tyr Tyr Ala Met Asp Tyr Trp Gly Gln
            100                 105                 110

Gly Thr Leu Val Thr Val Ser Ser
        115                 120


<210> SEQ ID NO 29
<211> LENGTH: 120
<212> TYPE: PRT
<213> ORGANISM: Artificial Sequence
<220> FEATURE:
<223> OTHER INFORMATION: Humanized antibody (T2H1)

<400> SEQUENCE: 29

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Ser Thr Tyr
            20                  25                  30

Val Met Ser Trp Val Arg Gln Ala Pro Gly Lys Gly Leu Glu Trp Val
        35                  40                  45

Ser Ser Ile Leu Ser Gly Gly Thr Ser Phe Tyr Ala Asp Asn Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Leu Tyr His Cys Ala
                85                  90                  95

Arg Arg Tyr Gly His Asp His Tyr Tyr Ala Met Asp Tyr Trp Gly Gln
            100                 105                 110

Gly Thr Thr Val Thr Val Ser Ser
        115                 120


<210> SEQ ID NO 30
<211> LENGTH: 120
<212> TYPE: PRT
<213> ORGANISM: Artificial Sequence
<220> FEATURE:
<223> OTHER INFORMATION: Humanized antibody (T2H2)

<400> SEQUENCE: 30

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Ser Thr Tyr
            20                  25                  30

Val Met Ser Trp Val Arg Gln Thr Pro Gly Lys Gly Leu Glu Trp Val
        35                  40                  45

Ser Ser Ile Leu Ser Gly Gly Thr Ser Phe Tyr Ala Asp Asn Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Leu Tyr His Cys Ala
                85                  90                  95
```

```
Arg Arg Tyr Gly His Asp His Tyr Tyr Ala Met Asp Tyr Trp Gly Gln
            100                 105                 110

Gly Thr Thr Val Thr Val Ser Ser
        115                 120


<210> SEQ ID NO 31
<211> LENGTH: 20
<212> TYPE: PRT
<213> ORGANISM: Artificial Sequence
<220> FEATURE:
<223> OTHER INFORMATION: IL-2 signal peptide

<400> SEQUENCE: 31

Met Tyr Arg Met Gln Leu Leu Ser Cys Ile Ala Leu Ser Leu Ala Leu
1               5                   10                  15

Val Thr Asn Ser
            20


<210> SEQ ID NO 32
<211> LENGTH: 288
<212> TYPE: PRT
<213> ORGANISM: Artificial Sequence
<220> FEATURE:
<223> OTHER INFORMATION: CD276 Fragment

<400> SEQUENCE: 32

Leu Glu Val Gln Val Pro Glu Asp Pro Val Val Ala Leu Val Gly Thr
1               5                   10                  15

Asp Ala Thr Leu Cys Cys Ser Phe Ser Pro Glu Pro Gly Phe Ser Leu
            20                  25                  30

Ala Gln Leu Asn Leu Ile Trp Gln Leu Thr Asp Thr Lys Gln Leu Val
        35                  40                  45

His Ser Phe Ala Glu Gly Gln Asp Gln Gly Ser Ala Tyr Ala Asn Arg
    50                  55                  60

Thr Ala Leu Phe Pro Asp Leu Leu Ala Gln Gly Asn Ala Ser Leu Arg
65                  70                  75                  80

Leu Gln Arg Val Arg Val Ala Asp Glu Gly Ser Phe Thr Cys Phe Val
                85                  90                  95

Ser Ile Arg Asp Phe Gly Ser Ala Ala Val Ser Leu Gln Val Ala Ala
            100                 105                 110

Pro Tyr Ser Lys Pro Ser Met Thr Leu Glu Pro Asn Lys Asp Leu Arg
        115                 120                 125

Pro Gly Asp Thr Val Thr Ile Thr Cys Ser Ser Tyr Arg Gly Tyr Pro
    130                 135                 140

Glu Ala Glu Val Phe Trp Gln Asp Gly Gln Gly Val Pro Leu Thr Gly
145                 150                 155                 160

Asn Val Thr Thr Ser Gln Met Ala Asn Glu Gln Gly Leu Phe Asp Val
                165                 170                 175

His Ser Val Leu Arg Val Val Leu Gly Ala Asn Gly Thr Tyr Ser Cys
            180                 185                 190

Leu Val Arg Asn Pro Val Leu Gln Gln Asp Ala His Gly Ser Val Thr
        195                 200                 205

Ile Thr Gly Gln Pro Met Thr Phe Pro Pro Glu Ala Leu Trp Val Thr
    210                 215                 220

Val Gly Leu Ser Val Cys Leu Ile Ala Leu Leu Val Ala Leu Ala Phe
225                 230                 235                 240

Val Cys Trp Arg Lys Ile Lys Gln Ser Cys Glu Glu Glu Asn Ala Gly
                245                 250                 255
```

```
Ala Glu Asp Gln Asp Gly Glu Gly Glu Gly Ser Lys Thr Ala Leu Gln
            260                 265                 270

Pro Leu Lys His Ser Asp Ser Lys Glu Asp Asp Gly Gln Glu Ile Ala
        275                 280                 285


<210> SEQ ID NO 33
<211> LENGTH: 316
<212> TYPE: PRT
<213> ORGANISM: Artificial Sequence
<220> FEATURE:
<223> OTHER INFORMATION: CD276 Fragment

<400> SEQUENCE: 33

Met Leu Arg Arg Arg Gly Ser Pro Gly Met Gly Val His Val Gly Ala
1               5                   10                  15

Ala Leu Gly Ala Leu Trp Phe Cys Leu Thr Gly Ala Leu Glu Val Gln
            20                  25                  30

Val Pro Glu Asp Pro Val Val Ala Leu Val Gly Thr Asp Ala Thr Leu
        35                  40                  45

Cys Cys Ser Phe Ser Pro Glu Pro Gly Phe Ser Leu Ala Gln Leu Asn
    50                  55                  60

Leu Ile Trp Gln Leu Thr Asp Thr Lys Gln Leu Val His Ser Phe Ala
65                  70                  75                  80

Glu Gly Gln Asp Gln Gly Ser Ala Tyr Ala Asn Arg Thr Ala Leu Phe
                85                  90                  95

Pro Asp Leu Leu Ala Gln Gly Asn Ala Ser Leu Arg Leu Gln Arg Val
            100                 105                 110

Arg Val Ala Asp Glu Gly Ser Phe Thr Cys Phe Val Ser Ile Arg Asp
        115                 120                 125

Phe Gly Ser Ala Ala Val Ser Leu Gln Val Ala Ala Pro Tyr Ser Lys
    130                 135                 140

Pro Ser Met Thr Leu Glu Pro Asn Lys Asp Leu Arg Pro Gly Asp Thr
145                 150                 155                 160

Val Thr Ile Thr Cys Ser Ser Tyr Arg Gly Tyr Pro Glu Ala Glu Val
                165                 170                 175

Phe Trp Gln Asp Gly Gln Gly Val Pro Leu Thr Gly Asn Val Thr Thr
            180                 185                 190

Ser Gln Met Ala Asn Glu Gln Gly Leu Phe Asp Val His Ser Val Leu
        195                 200                 205

Arg Val Val Leu Gly Ala Asn Gly Thr Tyr Ser Cys Leu Val Arg Asn
    210                 215                 220

Pro Val Leu Gln Gln Asp Ala His Gly Ser Val Thr Ile Thr Gly Gln
225                 230                 235                 240

Pro Met Thr Phe Pro Pro Glu Ala Leu Trp Val Thr Val Gly Leu Ser
                245                 250                 255

Val Cys Leu Ile Ala Leu Leu Val Ala Leu Ala Phe Val Cys Trp Arg
            260                 265                 270

Lys Ile Lys Gln Ser Cys Glu Glu Glu Asn Ala Gly Ala Glu Asp Gln
        275                 280                 285

Asp Gly Glu Gly Glu Gly Ser Lys Thr Ala Leu Gln Pro Leu Lys His
    290                 295                 300

Ser Asp Ser Lys Glu Asp Asp Gly Gln Glu Ile Ala
305                 310                 315
```